United States Patent
McNeel et al.

(10) Patent No.: US 9,827,308 B2
(45) Date of Patent: Nov. 28, 2017

(54) MINI-INTRONIC PLASMID DNA VACCINES IN COMBINATION WITH LAG3 BLOCKADE

(71) Applicant: Wisconsin Alumni Research Foundation, Madison, WI (US)

(72) Inventors: Douglas McNeel, Madison, WI (US); Viswa Colluru, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/964,717

(22) Filed: Dec. 10, 2015

(65) Prior Publication Data

US 2016/0166686 A1 Jun. 16, 2016

Related U.S. Application Data

(60) Provisional application No. 62/089,939, filed on Dec. 10, 2014.

(51) Int. Cl.
| | |
|---|---|
| A61K 39/395 | (2006.01) |
| A61K 39/00 | (2006.01) |
| A61K 39/39 | (2006.01) |
| C12N 15/85 | (2006.01) |

(52) U.S. Cl.
CPC ...... *A61K 39/3955* (2013.01); *A61K 39/0005* (2013.01); *A61K 39/0011* (2013.01); *A61K 39/39* (2013.01); *C12N 15/85* (2013.01); *A61K 2039/53* (2013.01); *A61K 2039/55516* (2013.01); *C12N 2800/101* (2013.01); *C12N 2800/24* (2013.01); *C12N 2800/30* (2013.01)

(58) Field of Classification Search
CPC . A61K 39/0011; A61K 39/39; A61K 2039/53
See application file for complete search history.

(56) References Cited

U.S. PATENT DOCUMENTS

| | | | |
|---|---|---|---|
| 7,179,797 B2 | 2/2007 | McNeel | |
| 2004/0214392 A1 | 10/2004 | Nabatame | |
| 2005/0118186 A1* | 6/2005 | Chiang | A61K 39/0011 424/185.1 |
| 2011/0150892 A1 | 6/2011 | Thudium | |
| 2013/0210897 A1 | 8/2013 | Kay | |
| 2013/0295110 A1* | 11/2013 | Binder | A61K 39/0011 424/142.1 |
| 2014/0093500 A1 | 4/2014 | Baeumont | |

FOREIGN PATENT DOCUMENTS

| | | |
|---|---|---|
| EP | 0893507 | 1/1999 |
| WO | 2010/019570 A2 | 2/2010 |
| WO | 2013/119371 A2 | 8/2013 |
| WO | 2014/008218 A1 | 1/2014 |

OTHER PUBLICATIONS

Zhang et al. Intratumoral T cells, recurrence, and survival in epithelial ovarian cancer. New England Journal of Medicine, vol. 348, pp. 203-213, Jan. 2003.*
Goldberg et al. LAG-3 in Cancer Immunotherapy. Cancer Immunology and Immunotherapy, vol. 344, pp. 269-278, 2011, published online Nov. 18, 2010.*
Oliveira et al. Marker-free plasmids for biotechnological applications—implications and perspectives. Trends in Biotechnology, vol. 31, No. 9, pp. 539-547, Sep. 2013.*
Matsuzaki et al. Tumor-infiltrating NY-ESO-1-specific CD8+ T cells are negatively regulated by LAG-3 and PD-1 in human ovarian cancer. Proceedings of the National Academy of Sciences, USA, vol. 107, No. 17, pp. 7875-7880, Apr. 2010.*
Blackburn, et al., Coregulation of CD8+ T cell exhaustion by multiple inhibitory receptors during chronic viral infection, Nature Immunol., 2009, 10, 29-37.
Blanchard, et al., Galectin-3 inhibitors: a patent review (2008-present), Expert Opin. Ther. Pat., 2014, 24, 1053-1065.
Chen, et al., Silencing of episomal transgene expression by plasmid bacterial DNA elements in vivo, Gene Ther., 2004; 11, 856-864.
Darquet, et al., Minicircle: an improved DNA molecule for in vitro and in vivo gene transfer, Gene Ther., 1999, 6, 209-218.
Dietz, et al., Minicircle DNA is superior to plasmid DNA in eliciting antigen-specific CD8+ T-cell responses, Mol. Ther., 2013, 21, 1526-1535.
Glinsky, et al., Synthetic galectin-3 inhibitor increases metastatic cancer cell sensitivity to taxol-induced apoptosis in vitro and in vivo, Neoplasia, 2009, 11, 901-909.
Grosso, et al., LAG-3 regulates CD8+ T-cell accumulation and effector function in murine self- and tumor-tolerance systems, J. Clin. Invest., 2007, 117, 3383-3392.
Grosso, et al., Functionally distinct LAG-3 and PD-1 subsets on activated and chronically stimulated CD8 T cells, J. Immunol., 2009, 182, 6659-6669.
Huang, C. T., Role of LAG-3 in regulatory T cells, Immunity, 2004, 21, 503-513.
Kouo, et al., Galectin-3 shapes antitumor immune responses by suppressing CD8+ T cells via LAG-3 and inhibiting expansion of plasmacytoid dendritic Cells, Cancer Immun. Res., 2015, 3(4), 412-423.
Liu, et al., DNA, vaccines: an historical perspective and view to the future, Immunol. Rev., 2011, 239(1), 62-84.

(Continued)

*Primary Examiner* — Jennifer Dunston
(74) *Attorney, Agent, or Firm* — Quarles & Brady LLP; Bennett J. Berson

(57) ABSTRACT

It is disclosed herein that (a) an anti-tumor DNA vaccine delivered using a MIP DNA vector is a less effective tumor treatment than the corresponding anti-tumor DNA vaccine delivered using a conventional pDNA vector, despite the MIP DNA vector eliciting a higher frequency of antigen-specific CD8+ T cells; and (b) tumor infiltrating CD8+ T cells in animals immunized with the MIP DNA vector express higher levels of the immune checkpoint protein LAG-3 than animals immunized with a conventional pDNA vector, while the expression levels of other immune checkpoint proteins was the same for both groups. Based on these findings, improved methods and compositions for administering DNA vaccines are disclosed. Specifically, DNA vaccines delivered with MIP DNA are administered along with a LAG-3 pathway blocking agent, resulting in a more effective vaccine-induced cellular immune response.

6 Claims, 26 Drawing Sheets
(19 of 26 Drawing Sheet(s) Filed in Color)

(56) References Cited

OTHER PUBLICATIONS

Lu, et al., The extragenic spacer length between the 5' and 3' ends of the transgene expression cassette affects transgene silencing from plasmid-based vectors, Mol. Ther., 2012, 20, 2111-2119.

Lu, et al., A mini-intronic plasmid (MIP): a novel robust transgene expression vector in vivo and in vitro, Mol. Ther., 2013, 21, 954-963.

Olson, et al., HLA-A2-restricted T-cell epitopes specific for prostatic acid phosphatase. Cancer Immunol. Immunother., 2010, 59, 943-953.

Olson, et al., CD8+ T cell specific for the androgen receptor are common in patients with prostate cancer and are able to lyse prostate tumor cells, Cancer Immunol. Immunoth., 2011, 60, 781-792.

Pardoll, M. D., The blockade of immune checkpoints in cancer immunotherapy, Nature Reviews—Cancer, 2012, 12, 252-264.

Rabinovich, et al., Immunosupressive stratagies that are mediated by tumor cells, Annual Review of Immunology, 2007, 25, 267-269.

Smith and McNeel, Vaccines targeting the cancer-testis antigen SSX-2 elicit HLA-A2 epitope-specific cytolytic T cells, J. Immunother., 2011, 34, 569-580.

Woo, et al., Immune inhibitory molecules LAG-3 and PD-1 synergistically regulate T-cell function to promote tumoral immune escape, Cancer Res., 2012, 72, 917-927.

Yu, et al., Genetic and pharmacological inhibition of galectin-3 prevents cardiac remodeling by interfering with myocardial fibrogenesis, Circ. Heart Fail, 2013, 6, 107-117.

Cappello, et al., LAG-3 enables DNA vaccination to persistently prevent mammary carcinogenesis in HER-2/neu transgenic BALB/c mice, Cancer Research, 2003, 63(10), 2518-2525.

International Search Report PCT/US2015/064959, dated Mar. 29, 2016.

\* cited by examiner

MINI-INTRONIC PLASMID DNA VACCINES IN COMBINATION WITH LAG3 BLOCKADE

CROSS-REFERENCE TO RELATED APPLICATIONS

This application claims the benefit of U.S. provisional Application No. 62/089,939 filed on Dec. 10, 2014, which is incorporated by reference herein in its entirety.

STATEMENT REGARDING FEDERALLY SPONSORED RESEARCH OR DEVELOPMENT

This invention was made with government support under CA142608 awarded by the National Institutes of Health. The government has certain rights in the invention.

BACKGROUND OF THE INVENTION

An antigen is a molecule, often but not always a polypeptide, that is capable of stimulating an immune response against target cells containing the antigen. DNA vaccines are DNA vectors administered in vivo that encode a polypeptide antigen that is expressed by the target cell type. When DNA vaccines specifically target tumor cells, the antigen may be specific to or more highly expressed by the targeted tumor cells. An example of such an antigen is the ligand-binding domain of the androgen receptor (AR LBD), which is more highly expressed in prostate tumor cells than in other normal tissues, such as liver, muscle, bladder, or brain tissue.

When delivered as a vaccine, the vector DNA is taken up by antigen presenting cells and expressed within the antigen presenting cell to produce the antigen, which is subsequently presented to lymphocytes to elicit a cellular and/or humoral immune response. In the case of cellular immunity, the antigens produced within the antigen presenting cell are bound to major histocompatibility complex (MHC) class I and II molecules and brought to the surface of the antigen presenting cell along with the MHC molecules. These surface antigens are then presented to immature T cells containing the cluster of differentiation 8 transmembrane glycoprotein (CD8+ T cells) and CD4+ cells. In the case of MHC class I presentation, this can result in the activation of the immature CD8+ T cells into mature antigen-specific CD8+ T cells (also known as cytolytic T cells or killer T cells), which subsequently target and kill the cell type expressing the antigen.

In clinical studies of DNA vaccines, the DNA vector is typically an engineered circular bacterial plasmid (pDNA) that includes both an expression cassette for the polypeptide of interest (e.g., the antigen) and a plasmid backbone. The expression cassette includes the DNA coding for the polypeptide of interest, as well as regulatory sequences that control the expression of the polypeptide. Such regulatory sequences may include, for example, a promoter sequence located upstream from (i.e., in the 5' direction from) the region coding for the polypeptide of interest. The plasmid backbone is the DNA sequence located between the two ends of the expression cassette, and includes elements present in the native bacterial plasmid, such as an origin of replication and a selectable marker. Such selectable markers may include, for example, an antibiotic resistance gene.

Notably, expression of the polypeptide of interest by the cells that take up the pDNA wanes with time, even if the plasmid itself persists within the cells. Such decreased expression, sometimes referred to as gene silencing, occurs within hours to days (see Darquet, A. M., Rangara, R., Kreiss, P., Schwartz, B., Naimi, S., Delaere, P., Crouzet, J. and Scherman, D. (1999) Minicircle: an improved DNA molecule for in vitro and in vivo gene transfer, *Gene Ther* 6: 209-18; Chen, Z. Y., He, C. Y., Meuse, L. and Kay, M. A. (2004), Silencing of episomal transgene expression by plasmid bacterial DNA elements in vivo, *Gene Ther* 11: 856-64). This decreased expression of the polypeptide of interest over time has been attributed to deposition of repressive heterochromatin on the plasmid backbone sequences required for plasmid propagation (see Chen, Z. Y., Riu, E., He, C. Y., Xu, H. and Kay, M. A. (2008), Silencing of episomal transgene expression in liver by plasmid bacterial backbone DNA is independent of CpG methylation, *Mol Ther* 16: 548-56).

This decreased expression over time of the polypeptide coded by the pDNA can be alleviated by using DNA minicircles (MCs) devoid of the majority of the plasmid backbone, instead of pDNA, as the DNA vector. This approach is described in detail in U.S. Patent Publication 2004/0214392, which is incorporated by reference herein in its entirety. Recent research using a listeriosis model demonstrated that using DNA MC-based vaccines as an alternative to conventional pDNA-based vaccines resulted in greater immunoprotection against *Listeria monocytogenes* expressing the MC-encoded antigen (see Dietz, W. M., Skinner, N. E. B., Hamilton, S. E., Jund, M. D., Heitfeld, S. M., Litterman, A. J., Hwu, P., Chen, Z., Salazar, A. M., Ohlfest, J. R., Blazar, B. R., Pennell, C. A., and Osborn, M. J. (2013), Minicircle DNA is superior to plasmid DNA in eliciting antigen-specific CD8+ T-cell responses, *Mol Ther* 21: 1526-1535). However, DNA minicircle vectors are difficult to produce in sufficient quantities for large scale clinical applications, because their production requires growth and propagation as a standard plasmid, and then site specific recombination and excision to produce the minicircle.

Recent research has shown that the decreased expression over time of polypeptides encoded by pDNA correlates with extragenic DNA spacer length within the vector. Specifically, gene silencing is caused by the length of the DNA between the 3' end of the region coding for the polypeptide of interest and the 5' end of the promoter that is operably linked to the coding region (i.e., the length of the DNA outside of the expression cassette), rather than being caused by any specific bacterial DNA sequences contained within the plasmid backbone (Lu, J., Zhang, F., Xu, S., Fire, A. Z. and Kay, M. A. (2012), The Extragenic Spacer Length Between the 5' and 3' Ends of the Transgene Expression Cassette Affects Transgene Silencing From Plasmid-based Vectors, *Mol Ther* 20: 2111-2119). Accordingly, an alternative DNA vector known as a mini-intronic plasmid (MIP) has been developed, in which the essential bacterial elements for plasmid replication and selection that are included in the plasmid backbone of conventional pDNA (i.e., the bacterial origin of replication and the selectable marker) are placed within an engineered intron within the expression cassette. This approach is described in detail in U.S. Patent Publication 2013/0210897, which is incorporated by reference herein in its entirety.

As with DNA minicircle vectors, using MIP vectors does not result in reduced expression over time of the polypeptide of interest, as seen with conventional pDNA vectors. Furthermore, using such vectors results in significantly increased expression of the polypeptide of interest, as compared to DNA minicircle vectors containing the same expression cassette. Finally, MIP vectors are relatively simple to produce (see Lu, J., Zhang, F. and Kay, M. A. (2013), A mini-intronic plasmid (MIP): a novel robust transgene expression vector in vivo and in vitro, *Mol Ther* 21: 954-63, which is incorporated by reference herein in its entirety).

DNA minicircle vectors and MIP vectors have not been previously used in vaccines specifically targeting tumors. The predicted efficacy of potential anti-tumor vaccines using such vectors is complicated by the complex and poorly understood mechanisms by which tumors co-opt certain immune checkpoint pathways to increase their resistance to attack by tumor antigen-specific CD8+ T cells.

Immune checkpoint pathways are T cell inhibitory pathways hardwired into the immune system. Immune checkpoint pathways function to maintain self-tolerance and to modulate the duration and amplitude of immune responses in peripheral tissues, in order to minimize collateral tissue damage that may potentially be caused by an overly aggressive immune response. Immune checkpoint pathways are generally activated by interactions between specific T cell surface receptor proteins, also known as checkpoint proteins, and their ligands, which are generally soluble proteins or proteins bound to the membrane of antigen-presenting cells. Immune checkpoint ligands may be overexpressed in tumor microenvironments, thus activating the corresponding checkpoint pathway and consequently inhibiting T cell response to the tumor cells, and likely contributing to the remarkable ability of tumor cells to evade successful attack by the host's immune system. For a review of known immune checkpoint pathways, see Pardoll, D. M. (2012), The blockade of immune checkpoints in cancer immunotherapy, *Nature Reviews—Cancer* 12: 252-264, which is incorporated by reference herein in its entirety.

Lymphocyte activation gene 3 (LAG-3; also known as CD223) codes for one of many known immune checkpoint proteins. LAG-3's function as an immune checkpoint protein was first described in 2004, when it was shown to have a role in enhancing the function of regulatory T cells ($T_{Reg}$ cells), which function to suppress the immune responses of other cells (Huang, C. T. (2004), Role of LAG-3 in regulatory T cells, *Immunity* 21: 503-513). LAG-3 also inhibits $CD8^+$ T cell functions independently of its role on $T_{Reg}$ cells (Grosso, J. F. et al. (2007), LAG-3 regulates $CD8^+$ T cell accumulation and effector function in murine self- and tumor-tolerance systems, *J. Clin. Invest.* 117: 3383-3392).

LAG-3 is one of a number of immune checkpoint proteins that are coordinately upregulated on both $T_{Reg}$ cells and anergic (alive but functionally inactivated) T cells, and the simultaneous blockade of multiple immune checkpoint proteins can result in enhanced reversal of the T cell anergic state, relative to blockade of LAG-3 alone. In particular, LAG-3 and the immune checkpoint protein programmed cell death protein 1 (PD-1) are commonly co-expressed on anergic T cells (Blackburn, S. D. et al. (2009), Coregulation of $CD8^+$ T cell exhaustion by multiple inhibitory receptors during chronic viral infection, *Nature Immunol.* 10: 29-37; Grosso, J. F. et al. (2009), Functionally distinct LAG-3 and PD-1 subsets on activated and chronically stimulated CD8 T cells, *J. Immunol.* 182: 6659-6669). Recently, it has been shown that LAG-3 and PD-1 are extensively co-expressed on tumor-infiltrating CD4+ and CD8+ T cells in three distinct transplantable tumors, and that antibody-based blockade of both LAG-3 and PD-1 synergistically cured mice of established tumors that were largely resistant to single antibody treatment (Woo, S. R. et al. (2012), Immune inhibitory molecules LAG-3 and PD-1 synergistically regulate T-cell function to promote tumoral immune escape, *Cancer Res.* 72: 917-927).

Although immune checkpoint protein blockade, by, for example, administering an antibody that can bind to the immune check protein, is recognized as a promising general approach for activating a therapeutic antitumor immune response (see Pardoll, D. M. (2012), The blockade of immune checkpoints in cancer immunotherapy, *Nature Reviews—Cancer* 12: 252-264), the relationship between any of the known immune checkpoint pathways and the mechanisms of action of tumor-targeting DNA vaccines has not been studied. Specifically, it is not known how (if at all) using a specific DNA vector type as a vaccine may affect any of the known immune checkpoint pathways. Thus, no specific immune checkpoint blockade strategies would be expected to synergistically improve the therapeutic efficacy of DNA vaccines, whether delivered by pDNA, DNA minicircles, MIPs, or by any other DNA vector.

Accordingly, there is a need for methods and compositions developed from an improved understanding of the relationship between relevant immune checkpoint pathways and the specific vectors used for DNA vaccine delivery.

BRIEF SUMMARY

This disclosure is based on the surprising findings that (a) an anti-tumor DNA vaccine delivered using a MIP DNA vector is a less effective tumor treatment than the corresponding anti-tumor DNA vaccine delivered using a conventional pDNA vector, despite the increased antigen expression from the MIP DNA vector eliciting a higher frequency of antigen-specific CD8+ T cells; and (b) tumor infiltrating CD8+ T cells in animals immunized with the MIP DNA vector express higher levels of the immune checkpoint protein LAG-3 than animals immunized with a conventional pDNA vector, while the expression levels of other immune checkpoint proteins was the same for both groups. Based on these findings, the efficacy of DNA vaccines delivered using MIP DNA vectors can be synergistically improved by the simultaneous blockade of the LAG-3 immune checkpoint pathway.

Accordingly, in a first aspect, the disclosure encompasses a method for reducing the number of cells of a target cell type in a subject in need of such treatment to reduce the target cell type. The method includes the step of administering to the subject a mini-intronic plasmid (MIP) comprising (a) an expression cassette comprising a polynucleotide sequence encoding an antigen expressed by cells of the target cell type, and (b) an intron comprising a bacterial origin of replication and a selectable marker. This step results in the activation of antigen-specific CD8+ T cells against cells of the target cell type. However, the activated CD8+ T cells exhibit increased surface expression of the lymphocyte activation gene 3 (LAG-3) immune checkpoint protein, an inhibitor of the cell-mediated immune response.

To reduce the immunoinhibitory effects of increased LAG-3 expression, the method further includes the step of co-administering to the subject a LAG-3 immune checkpoint protein blocking agent. The LAG-3 immune checkpoint protein blocking agent reduces the immunoinhibitory effects of increased LAG-3 expression seen in the CD8+ T cells that are activated as a result of the first step. When these two steps are performed, the number of cells of the target cell type is synergistically decreased in the subject. In some embodiments, the method further includes administering a second checkpoint protein blocking agent.

Optionally, the method is performed without co-administering a second immune checkpoint protein blocking agent, such as, without limitation, a PD-1 checkpoint protein blocking agent.

In some embodiments, to reduce the immunoinhibitory effects of increased LAG-3 expression, the method includes the step of co-administering to the subject a LAG-3 immune checkpoint protein pathway blocking agent that blocks a protein or ligand of the LAG-3 immune checkpoint protein pathway. The LAG-3 immune checkpoint protein pathway blocking agent reduces the immunoinhibitory effects of increased LAG-3 expression seen in the CD8+ T cells that are activated as a result of the administration of the MIP by blocking and/or inhibiting the protein's or ligand's activity. In some embodiments, the protein is a LAG-3 binding partner. This inhibition of the protein's or ligand's activity results in the inhibition of the upregulation of LAG-3. In some embodiments, the LAG-3 ligand or binding partner that is inhibited is Galectin-3 or MHC-II. In some embodiments, the inhibitor of Galectin-3 or MHC-II may be co-administered in an effective amount to reduce the activation of LAG-3 expression in the CD8+ cells. When these two steps are performed, the number of cells of the target cell type is synergistically decreased in the subject. Optionally, the method is performed without co-administering a second immune checkpoint protein blocking agent, such as, without limitation, a programmed cell death protein 1 (PD-1) checkpoint protein blocking agent, T-cell immunoglobulin and mucin-domain containing-3 (TIM3) checkpoint protein blocking agent, V-domain Ig suppressor of T cell activation (VISTA) checkpoint protein blocking agent, cytotoxic T-lymphocyte-associated protein 4 (CTLA4) checkpoint protein blocking agent and the like.

In some embodiments, the intron is located in the expression cassette upstream of the polynucleotide sequence that encodes the antigen. In some embodiments, the expression cassette includes a promoter sequence at its 5' end. In some embodiments, the encoded antigen is synovial sarcoma X breakpoint 2 (SSX2), androgen receptor ligand-binding domain (AR LBD), prostate-specific antigen (PSA), human epidermal growth factor receptor 2 (HER-2/neu), or prostatic acid phosphatase (PAP) or fragments thereof. In some embodiments, the selectable marker is an antibiotic resistance gene.

In some embodiments, the LAG-3 immune checkpoint protein pathway blocking agent blocks LAG-3 pathway upstream of LAG-3 and results in a decrease in the expression of LAG-3 in the CD8+ cells. In some embodiments, the LAG-3 immune checkpoint protein pathway blocking agent is an inhibitor of an upstream protein or ligand of LAG-3. In some embodiments, the LAG-3 immune checkpoint protein pathway blocking agent is an inhibitor of or antibody that binds Galectin-3 or MHC-II which inhibit or reduce Galectin-3 or MHC-II interaction with LAG-3.

In some embodiments, the LAG-3 immune checkpoint protein blocking agent is an antibody that binds to LAG-3. In some embodiments, the LAG-3 immune checkpoint protein pathway blocking agent is an inhibitor of LAG-3.

In some embodiments, the target cell type is a cancer cell. In some such embodiments, the cancer cell is a prostate cancer cell, a malignant melanoma cell, a colon cancer cell, a liver cancer cell, a lung cancer cell, an ovarian cancer cell, a renal cancer cell, a pancreatic cancer cell, or a breast cancer cell.

In a second aspect, the disclosure encompasses a composition for reducing the number of cells of a target cell type. The composition includes a mini-intronic plasmid (MIP) comprising an expression cassette comprising (a) a polynucleotide sequence encoding an antigen expressed by cells of the target cell type, and (b) an intron comprising a selectable marker and a bacterial origin of replication; and a LAG-3 immune checkpoint protein pathway blocking agent. In some embodiments, the LAG-3 immune checkpoint protein pathway blocking agent is a LAG-3 immune checkpoint protein blocking agent. In some embodiments, the composition further includes a second checkpoint protein pathway blocking agent. In some embodiments, the second checkpoint protein pathway blocking agent is Programmed cell death protein 1 (PD-1), T-cell immunoglobulin and mucin-domain containing-3 (TIM3), V-domain Ig suppressor of T cell activation (VISTA), cytotoxic T-lymphocyte-associated protein 4 (CTLA4) and the like.

In some embodiments, the composition does not include a second checkpoint protein pathway blocking agent. For example, in some embodiments, the composition does not include a PD-1 immune checkpoint protein blocking agent. In some embodiments, the composition does not include a second checkpoint protein pathway blocking agent, wherein the second protein pathway blocking agent is PD-1, TIM3, VISTA, CTLA4 or the like.

In some embodiments, the intron is located in the expression cassette upstream of the polynucleotide sequence encoding the antigen. In some embodiments, the expression cassette includes a promoter sequence at its 5' end. In some embodiments, the encoded antigen is synovial sarcoma X breakpoint 2 (SSX2), androgen receptor ligand-binding domain (AR LBD), prostate-specific antigen (PSA), human epidermal growth factor receptor 2 (HER-2/neu), or prostatic acid phosphatase (PAP). In some embodiments, the selectable marker is an antibiotic resistance gene.

In some embodiments, the LAG-3 immune checkpoint protein blocking agent is an antibody that binds to LAG-3.

In some embodiments, the LAG-3 immune checkpoint protein pathway blocking agent blocks or inhibits a protein or ligand required for LAG-3 expression and results in a decrease or reduced expression of LAG-3 in the CD8+ T cells. In some embodiments, the LAG-3 immune checkpoint protein pathway blocking agent is an inhibitor of a ligand or binding partner of LAG-3. In some embodiments, the inhibitor may be a protein that binds the ligand or binding partner and inhibits interaction of the ligand or binding partner with LAG-3. The ligand or binding partner may be Galectin-3 or MHC-II.

In some embodiments, the LAG-3 immune checkpoint protein pathway blocking agent is an inhibitor of or antibody that binds to Galectin-3 or MHC-II.

In some embodiments, the target cell type is a cancer cell. In some such embodiments, the cancer cell is a prostate cancer cell, a malignant melanoma cell, a colon cancer cell, a liver cancer cell, a lung cancer cell, an ovarian cancer cell, a renal cancer cell, a pancreatic cancer cell, or a breast cancer cell.

In a third aspect, the disclosure encompasses a kit for reducing the number of cells of a target cell type in a subject. The kit includes a mini-intronic plasmid (MIP) comprising an expression cassette comprising (a) a polynucleotide sequence encoding an antigen expressed by cells of the target cell type, and (b) an intron containing a bacterial origin of replication and a selectable marker; and a LAG-3 immune checkpoint protein blocking agent or a LAG-3 immune checkpoint protein pathway blocking agent.

In some aspects, the kit includes a second checkpoint protein pathway blocking agent. In some embodiments, the second checkpoint protein pathway blocking agent is PD-1, TIM3, VISTA, CTLA4 and the like.

In some aspects, the kit does not include a second checkpoint protein pathway blocking agent. For example, in some aspects, the kit does not include a PD-1, TIM3, VISTA, CTLA4 or the like blocking agent. In some embodiments, the intron is located in the expression cassette upstream of the polynucleotide sequence encoding for the antigen. In some embodiments, the expression cassette includes a promoter sequence at its 5' end. In some embodiments, the encoded antigen is synovial sarcoma X breakpoint 2 (SSX2), androgen receptor ligand-binding domain (AR LBD), prostate-specific antigen (PSA), human epidermal growth factor receptor 2 (HER-2/neu), or prostatic acid phosphatase (PAP). In some embodiments, the antigen is a fragment or epitope of the antigen protein. In some embodiments, the selectable marker is an antibiotic resistance gene.

In some embodiments, the LAG-3 immune checkpoint protein blocking agent is an antibody that binds to LAG-3.

In some embodiments, the target cell type is a cancer cell. In some such embodiments, the cancer cell is a prostate cancer cell, a malignant melanoma cell, a colon cancer cell, a liver cancer cell, a lung cancer cell, an ovarian cancer cell, a renal cancer cell, a pancreatic cancer cell, or a breast cancer cell.

In a fourth aspect, the disclosure encompasses a composition comprising a mini-intronic plasmid (MIP) comprising an expression cassette comprising (a) a polynucleotide sequence encoding an antigen expressed by cells of a target cell type, and (b) an intron containing a bacterial origin of replication and a selectable marker; and a LAG-3 immune checkpoint protein blocking agent or a LAG-3 immune checkpoint protein pathway blocking agent. The composition is used to manufacture a medicament for reducing the number of cells of the target cell type in a subject in a subject in need of such treatment. In some embodiments, the composition further includes a second checkpoint protein pathway blocking agent. In some embodiments, the second checkpoint protein pathway blocking agent is PD-1, TIM3, VISTA, CTLA4 and the like.

In some embodiments, the composition optionally does not include a second checkpoint protein pathway blocking agent. For example, in some embodiments, the composition does not include a PD-1, TIM3, VISTA or CTLA4 immune checkpoint protein blocking agent.

In some embodiments, the intron is located in the expression cassette upstream of the polynucleotide sequence encoding for the antigen. In some embodiments, the expression cassette includes a promoter sequence at its 5' end. In some embodiments, the encoded antigen is synovial sarcoma X breakpoint 2 (SSX2), androgen receptor ligand-binding domain (AR LBD), prostate-specific antigen (PSA), human epidermal growth factor receptor 2 (HER-2/neu), or prostatic acid phosphatase (PAP). In some embodiments, the encoded antigen is a fragment or an epitope of the antigen. In some embodiments, the selectable marker is an antibiotic resistance gene.

In some embodiments, the LAG-3 immune checkpoint protein blocking agent is an antibody that binds to LAG-3.

In some embodiments, the target cell type is a cancer cell. In some such embodiments, the cancer cell is a prostate cancer cell, a malignant melanoma cell, a colon cancer cell, a liver cancer cell, a lung cancer cell, an ovarian cancer cell, a renal cancer cell, a pancreatic cancer cell, or a breast cancer cell.

In a fifth aspect, the disclosure encompasses a composition comprising a mini-intronic plasmid (MIP) comprising an expression cassette comprising (a) a polynucleotide sequence encoding an antigen expressed by cells of a target cell type, and (b) an intron containing a bacterial origin of replication and a selectable marker; and a LAG-3 immune checkpoint protein blocking agent. The composition is used to reduce the number of cells of the target cell type in a subject in need of such treatment. In some embodiments, the composition further includes a second checkpoint protein pathway blocking agent, for example, PD-1, TIM3, VISTA, CTLA4 or the like.

Optionally, in some embodiments, the composition does not include a second checkpoint protein blocking agent. For example, in some embodiments, the composition does not include PD-1, TIM3, VISTA, CTLA4 or the like immune checkpoint protein blocking agent.

In some embodiments, the intron is located in the expression cassette upstream of the polynucleotide sequence encoding for the antigen. In some embodiments, the expression cassette includes a promoter sequence at its 5' end. In some embodiments, the encoded antigen is synovial sarcoma X breakpoint 2 (SSX2), androgen receptor ligand-binding domain (AR LBD), prostate-specific antigen (PSA), human epidermal growth factor receptor 2 (HER-2/neu), or prostatic acid phosphatase (PAP). In some embodiments, the selectable marker is an antibiotic resistance gene.

In some embodiments, the LAG-3 immune checkpoint protein blocking agent is an antibody that binds to LAG-3.

In some embodiments, the target cell type is a cancer cell. In some such embodiments, the cancer cell is a prostate cancer cell, a malignant melanoma cell, a colon cancer cell, a liver cancer cell, a lung cancer cell, an ovarian cancer cell, a renal cancer cell, a pancreatic cancer cell, or a breast cancer cell.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Vaccines targeting the cancer-testis antigen SSX-2 elicit HLA-A2 epitope-specific cytolytic T cells. J Immunother. 2011; 34:569-80, which is incorporated by reference in its entirety. Thus, all three vectors have the exact same "expression construct" viz., promoter and transgene encoding elements, as the parent plasmid pTVG-SSX2. These plasmids have an ordinary stop codon to terminate transcription. The GFP constructs on the other hand, were made from this commercially available parent MC vector and as such, have the SV40 element. Plasmid maps of the relevant constructs are included as FIGS. 16-21.

Figure 2:
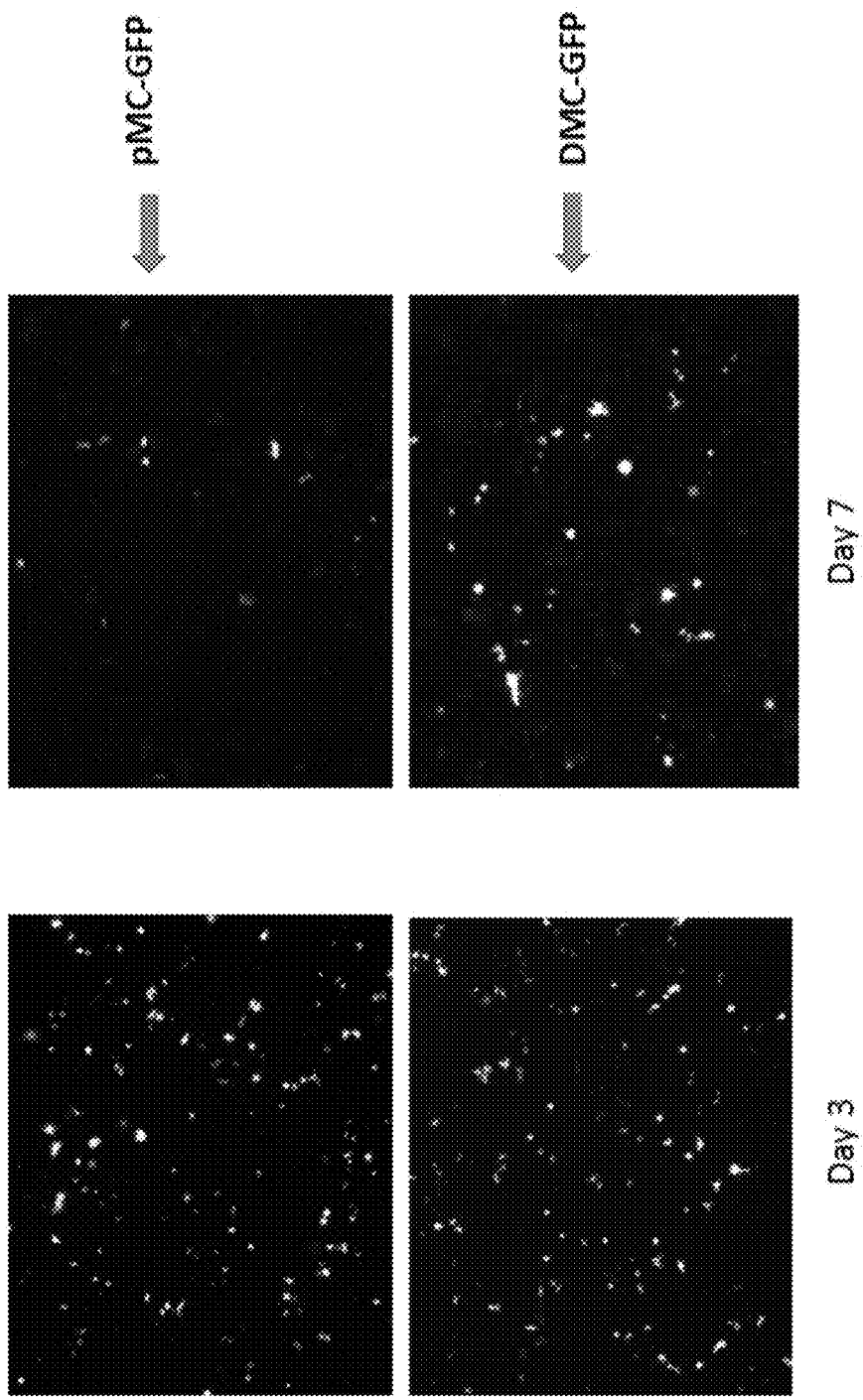

FIG. 2 includes fluorescence microscopy images of Cos7 cells that had taken up (i.e., been transfected with) two different vectors encoding green fluorescent protein (GFP), at three and seven days after transfection. Cos7 cells were transfected with either conventional plasmids encoding GFP as the polypeptide of interest (top panels; pMC-GFP), or DNA minicircle vectors encoding GFP as the polypeptide of interest (bottom panels; DMC-GFP). Images show GFP expression after three days (left panels) and 7 days (right panel). While expression of GFP was largely silenced after seven days in cells that had been transfected with the conventional plasmid (top right), expression was sustained in cells that had been transfected with the minicircle vector (bottom right).

Figure 3A:
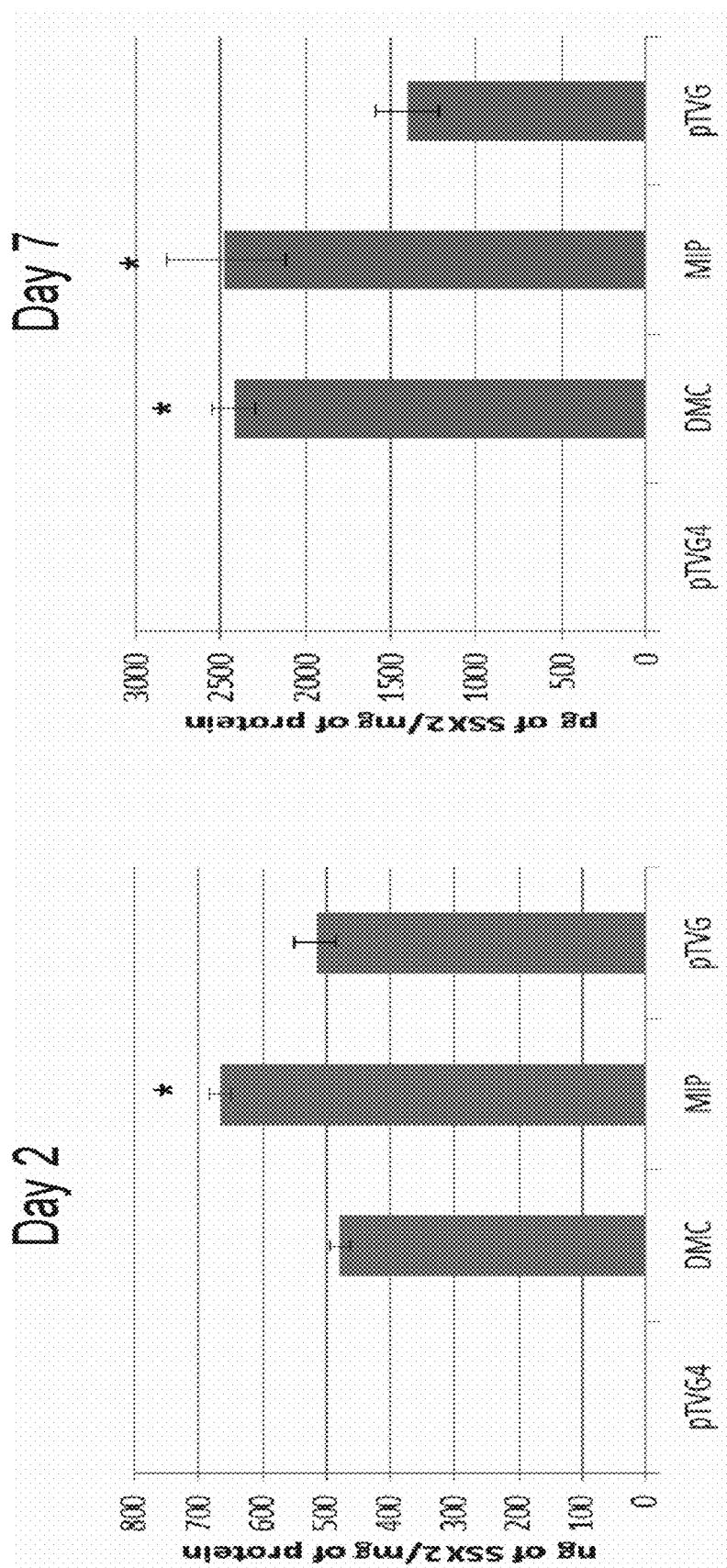

FIG. 3A includes bar graphs showing the amount of SSX2 protein contained in vector-transfected cells (per milligram of protein lysate), as measured by quantitative ELISA. LNCaP cells were transfected with equimolar amounts of conventional plasmid encoding SSX2 (pTVG), DNA minicircle vector encoding SSX2 (DMC), mini-intronic plasmid vector encoding SSX2 (MIP), or a plasmid vector control not encoding for SSX2 (pTVG4). Cells were lysed after 2 days (left panel) or 7 days (right panel), and evaluated for SSX2 protein expression. * Shows significant difference relative to pTVG plasmid ($p<0.05$).

Figure 3B:
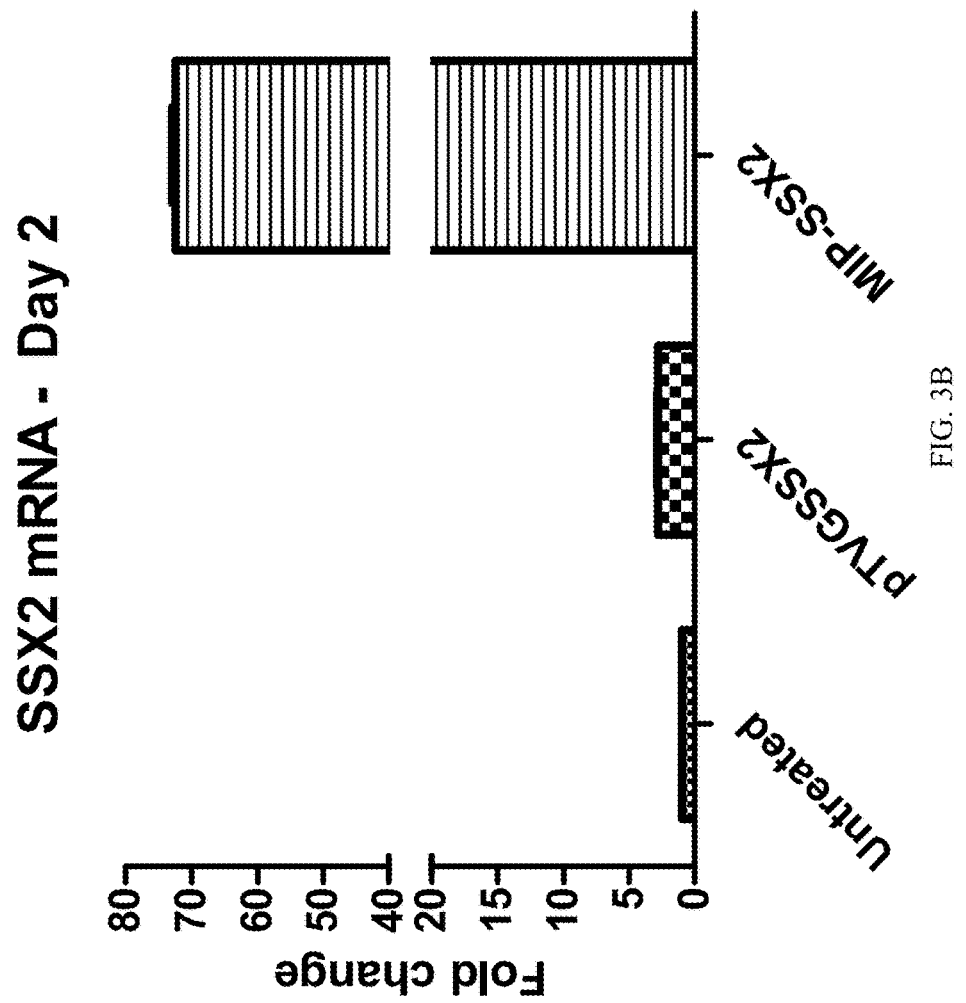

FIG. 3B is a graph depicting in vivo levels of SSX2 in a mouse model. Equimolar amounts of pTVG-SSX2 and MIP-SSX2 were injected intradermally in the ear of mice (n=2 per group) using a 28.5 gauge needle.

Figure 4:
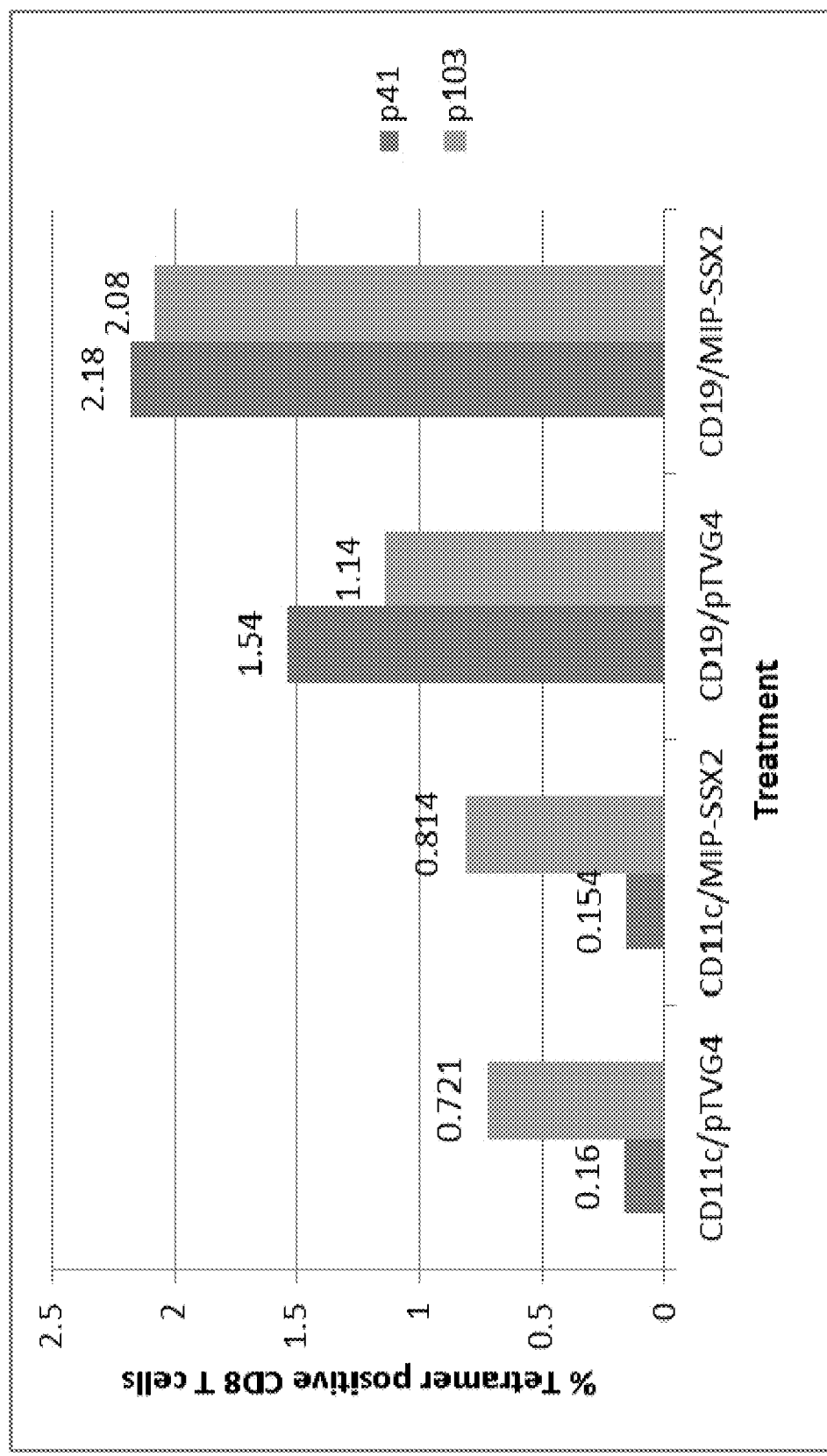

FIG. 4 is a bar graph showing the extent of SSX2-specific CD8+ T cells expansion using two different cell and vector types. CD11c+ dendritic cells and CD19+ B cell populations were enriched using STEMSEP® phycoerythrin (PE) selection and incubated with T-lymphocytes from an HLA-A2$^+$ patient known to have CD8+ T cells specific for HLA-A2-restricted p41 and p103 SSX2-specific epitopes. These cells were then treated with either a DNA vector lacking an SSX2 coding region (pTVG4), or a mini-intronic plasmid encoding SSX2 (MIP-SSX2), along with 0.5 ng/mL IL-1β and 10 U/mL IL-2 for 7 days, after which tetramer staining was performed. The numbers indicate the % of tetramer-positive cells among CD8+ T cells detectable after culture. Tetramer staining identifies the T cells present that are specific for the encoded antigen. The data shown demonstrate that using the MIP vector along with CD19+ B cells facilitates substantial expansion of mature antigen-specific CD8+ T cells, as compared to the pTVG4 control.

Figure 5A:
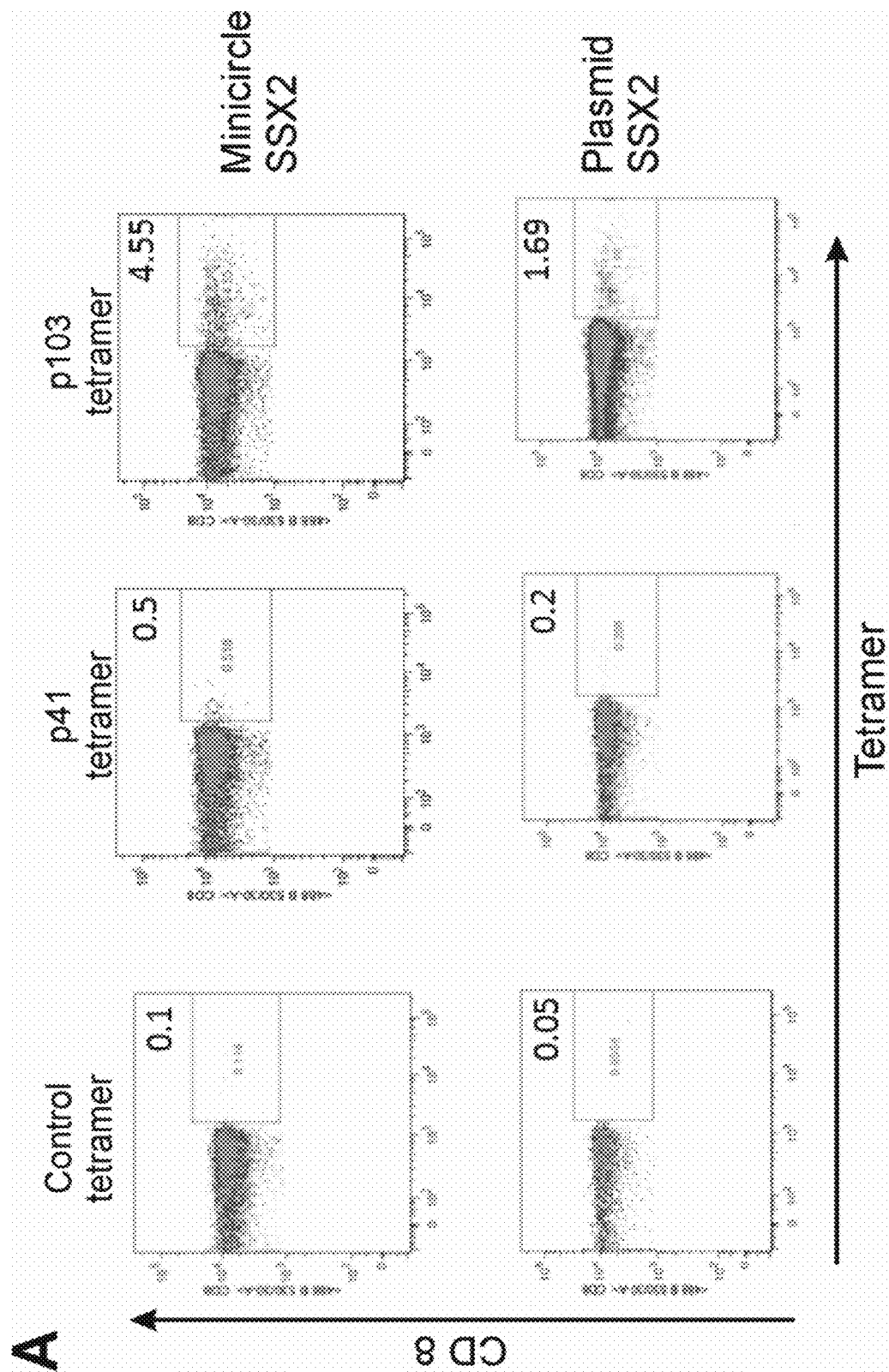

FIG. 5A shows flow cytometry data for splenocytes collected from immunized mice. HHD-II mice were immunized four times at 2-week intervals with plasmid DNA encoding SSX2 (pTVG-SSX2), DNA minicircle encoding SSX2 (DMC-SSX2), or vector control (pTVG4). Splenocytes were collected, pooled, and assessed for the frequency of SSX2 tetramer-specific CD3+CD8+ gated T cells (p103=dominant epitope, p41=subdominant epitope, pp11=control). Immunization with the DNA minicircles elicited the highest frequency of antigen-specific CD8+ T cells.

Figure 5B:
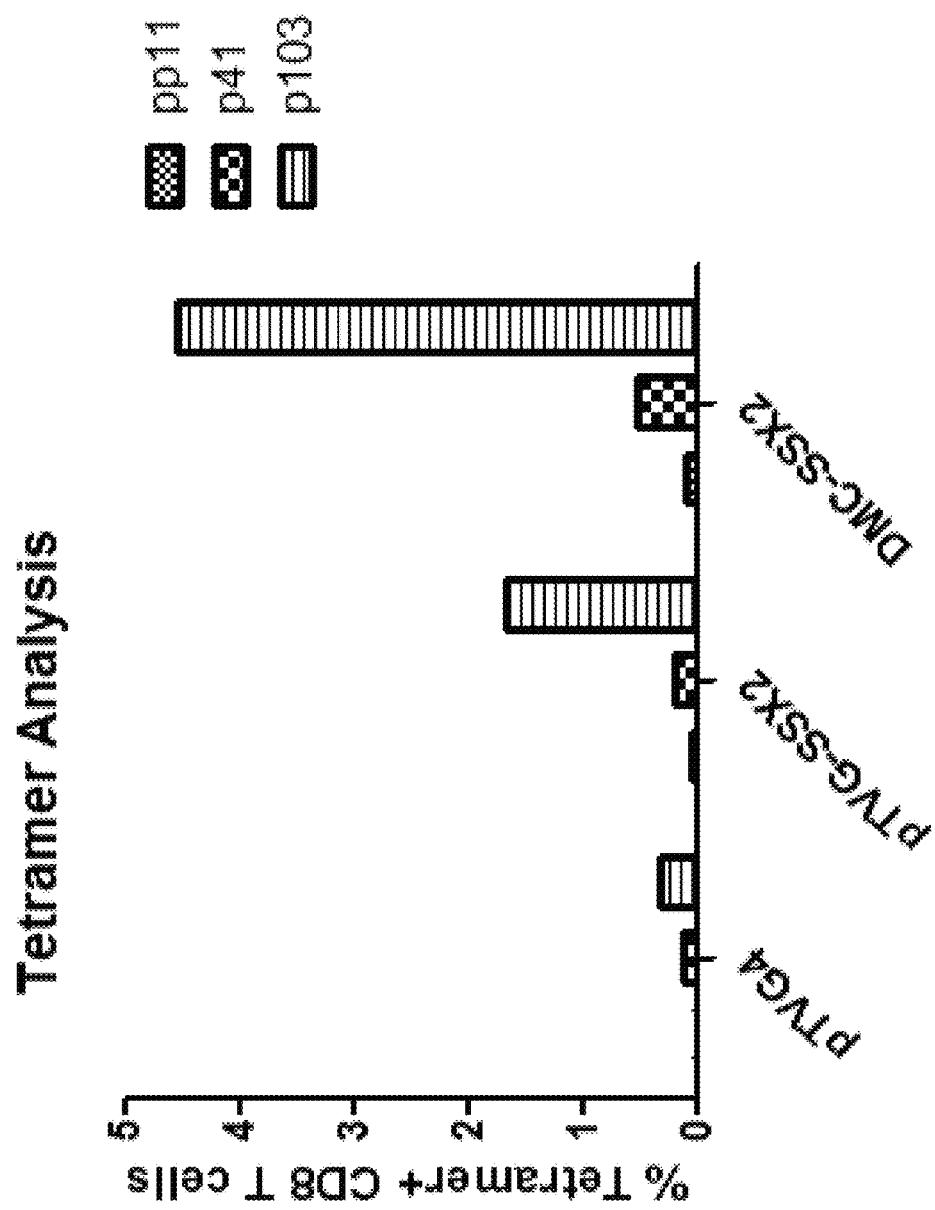

FIG. 5B shows a bar graph of the flow cytometry data for splenocytes collected from immunized mice. HHD-II mice were immunized four times at 2-week intervals with plasmid DNA encoding SSX2 (pTVG-SSX2), DNA minicircle encoding SSX2 (DMC-SSX2), or vector control (pTVG4). Splenocytes were collected, pooled, and assessed for the frequency of SSX2 tetramer-specific CD3+CD8+ gated T cells (p103=dominant epitope, p41=subdominant epitope, pp11=control). Immunization with the DNA minicircles elicited the highest frequency of antigen-specific CD8+ T cells.

Figure 6:
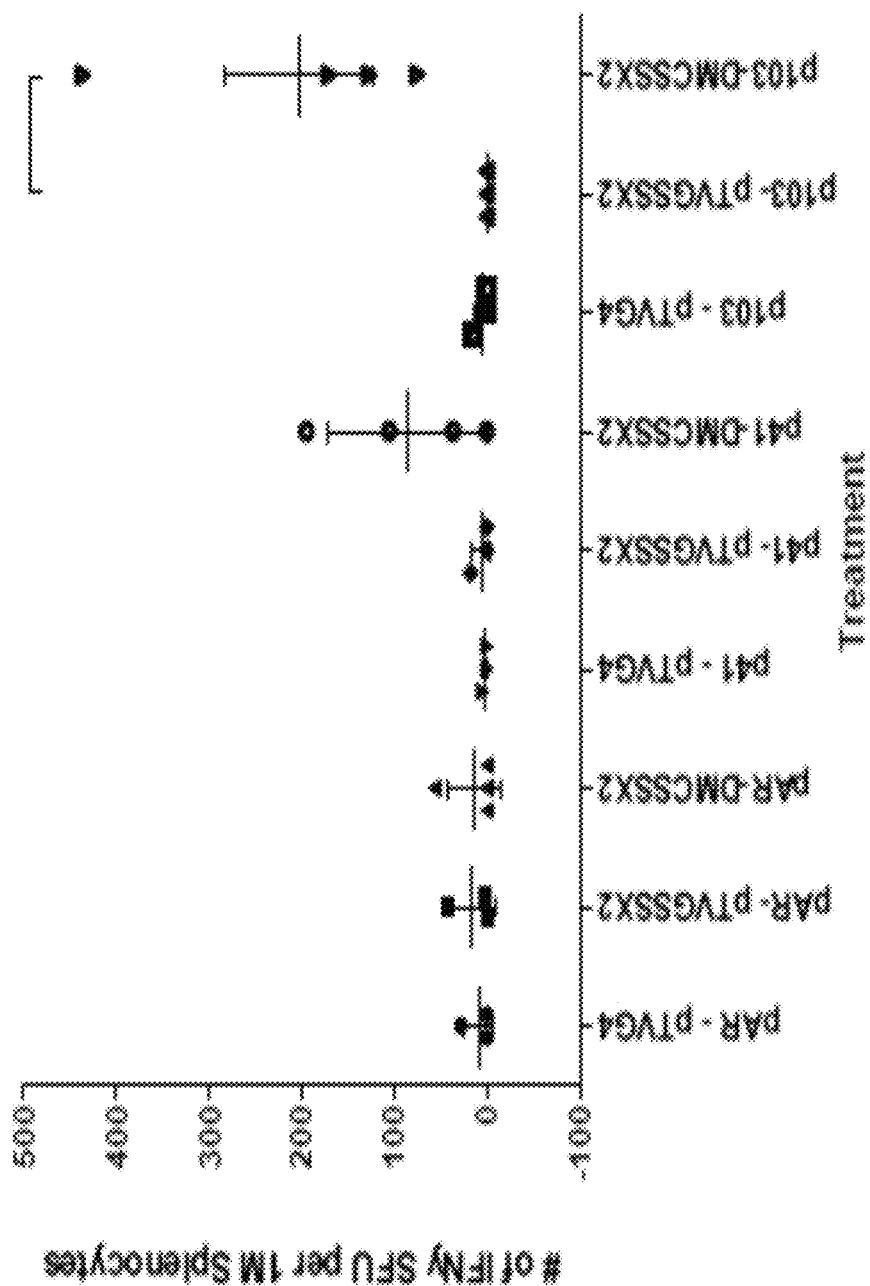

FIG. 6 is a graph showing SSX2 epitope-specific IFNγ release in splenocytes collected from immunized mice. HHD-II mice were immunized four times at 2-week intervals with plasmid DNA encoding SSX2 (pTVG-SSX2), DNA minicircles encoding SSX2 (DMC-SSX2), or vector control (pTVG4). Splenocytes were collected and assessed for SSX2 epitope specific IFNγ release. p103=dominant epitope, p41=subdominant epitope, pAR is androgen receptor (control). Data is represented as frequency of IFN-gamma producing cells per 1 million splenocytes. Each data point represents splenocytes from one animal.

Figure 7:
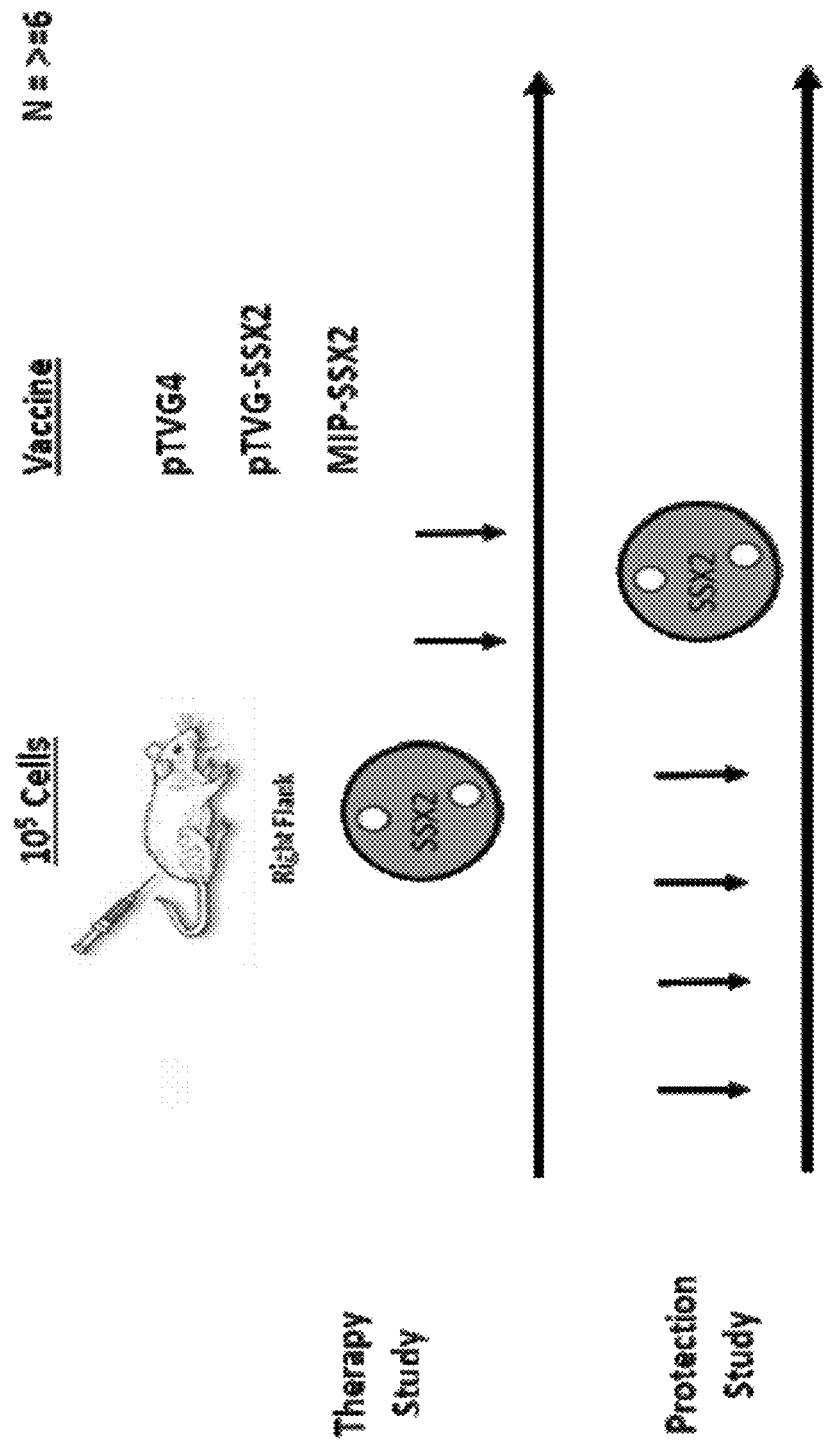

FIG. 7 is a schematic diagram illustrating the tumor model study design used in Example 2 and Example 3. HLA-A2 expressing mice were implanted subcutaneously with $10^5$ A2/Sarcoma cells expressing SSX2 on Day 0, and subsequently immunized two times at 2-week intervals (on Days 1 and 15) with plasmid DNA encoding SSX2 (pTVG-SSX2), mini-intronic plasmids encoding SSX2 (MIP-SSX2), or vector control (pTVG4) in a therapeutic setting (top). For the protection study (bottom), HLA-A2 expressing mice were first immunized four times (day 0, 13, 26, 39) at 2-week intervals with pTVG-SSX2 or pTVG4 and subsequently challenged with $5*10^4$ A2/Sarcoma cells expressing SSX2 on day 52 to assay for anti-tumor efficacy of the different constructs.

Figure 8A:
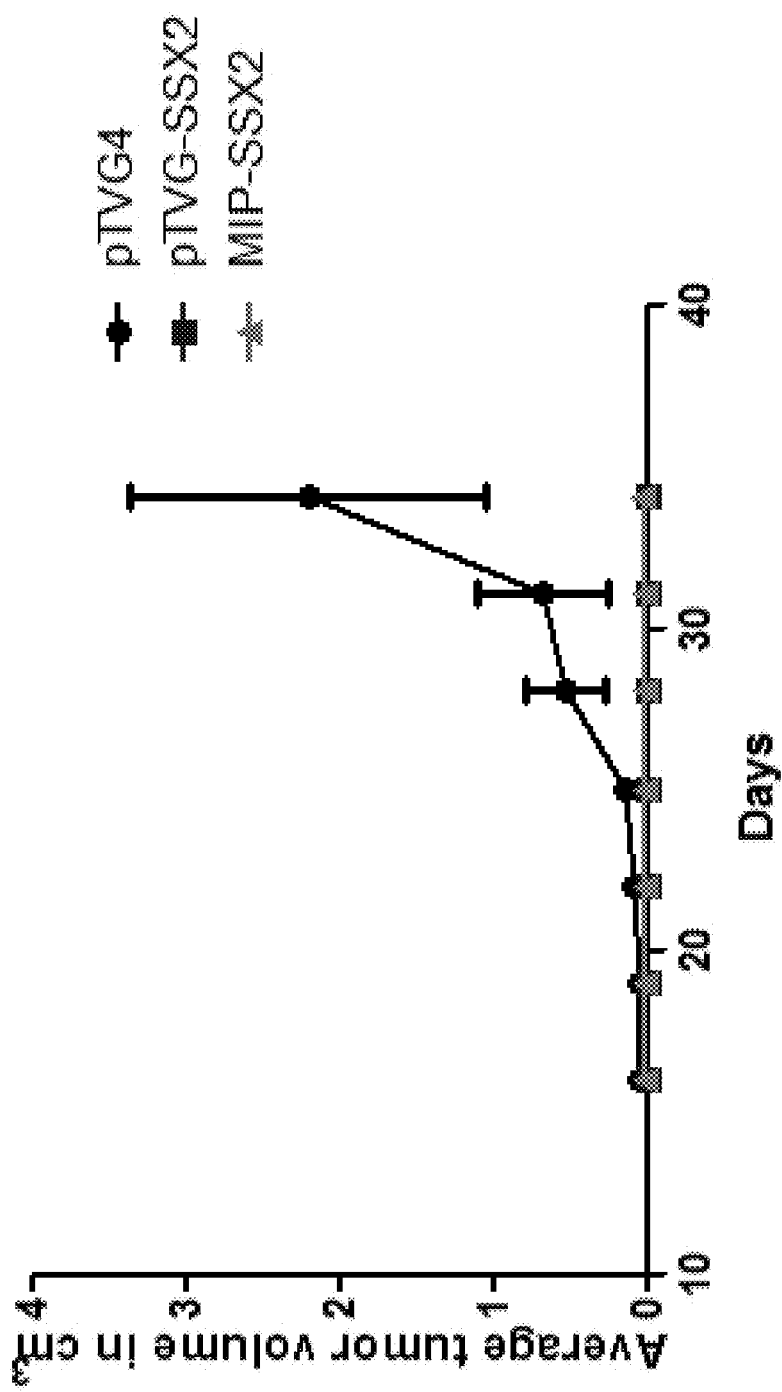

FIG. 8A is a graph depicting the average tumor volume after immunizing with MIP-SSX2 or plasmid DNA encoding SSX2 (pTVG-SSX2) (or pTVG4) prior to implantation with tumor cells in a prophylactic setting.

Figure 8B:
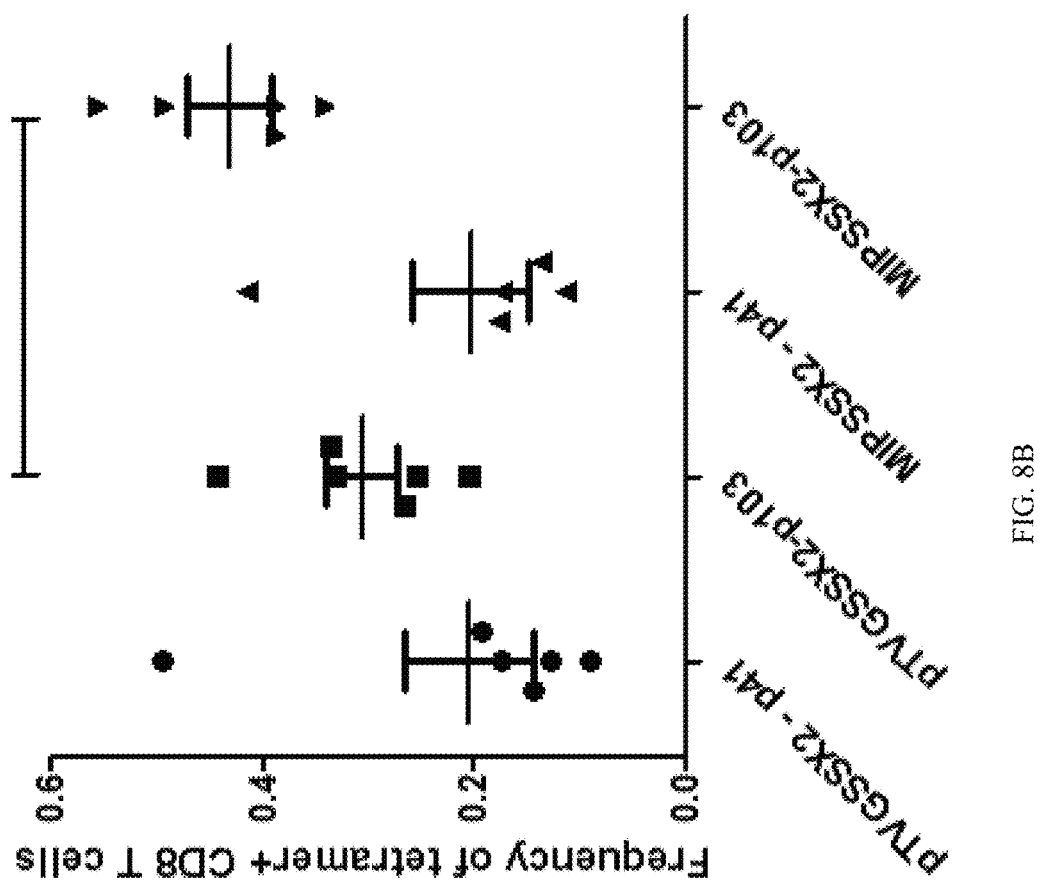

FIG. 8B is a graph depicting the frequency of tetramer CD8+ T cells after prophylactic immunization.

Figure 9A:
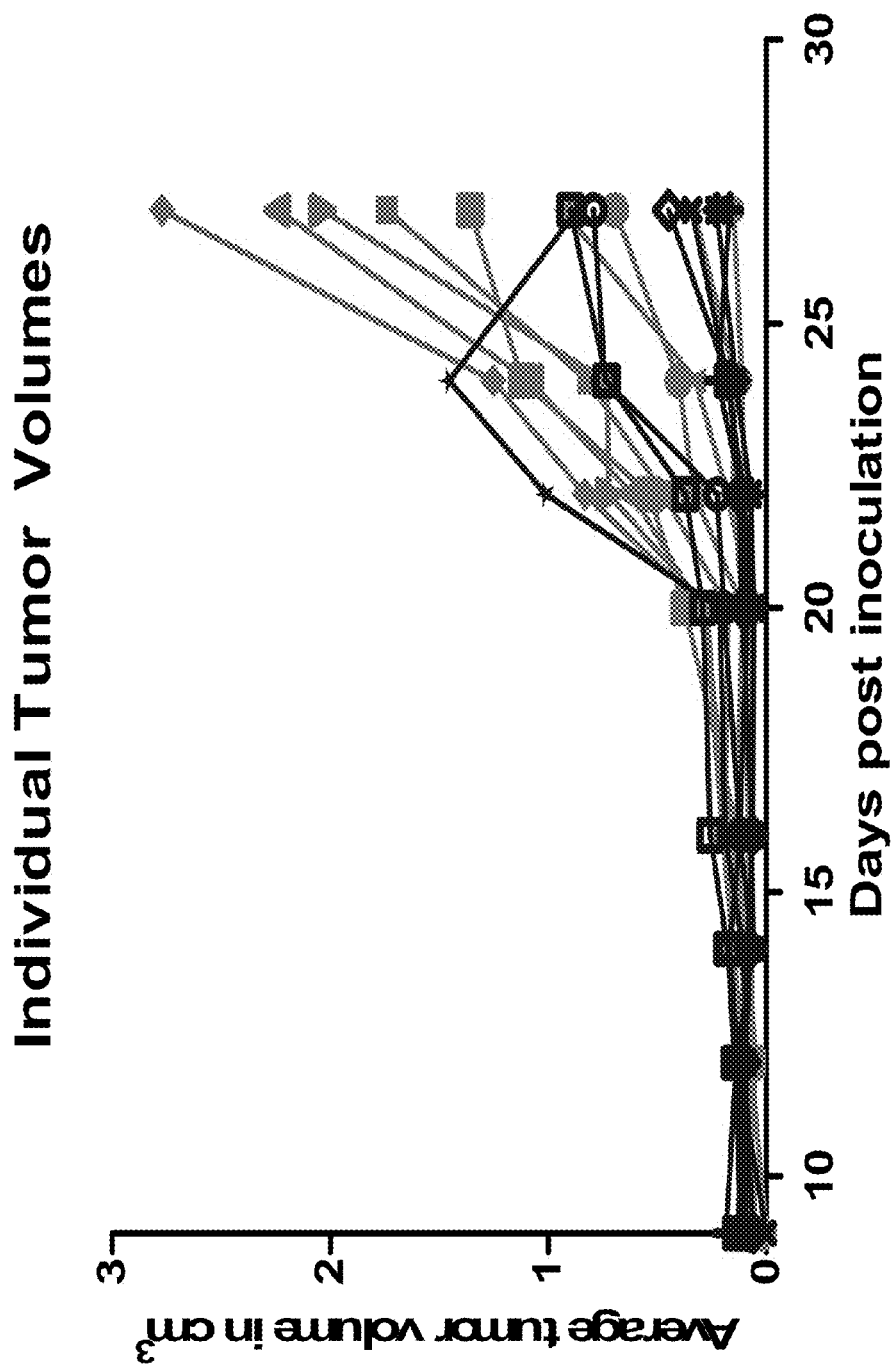

FIG. 9A shows individual tumor growth curves obtained from the study described in FIG. 7. The leftmost eight curves were obtained from mice immunized with pTVG-SSX2, and the rightmost nine curves were obtained from mice immunized with MIP-SSX2. Surprisingly, mice immunized with MIP-SSX2 generally exhibited greater tumor growth than mice immunized with pTVG-SSX2.

Figure 9B:
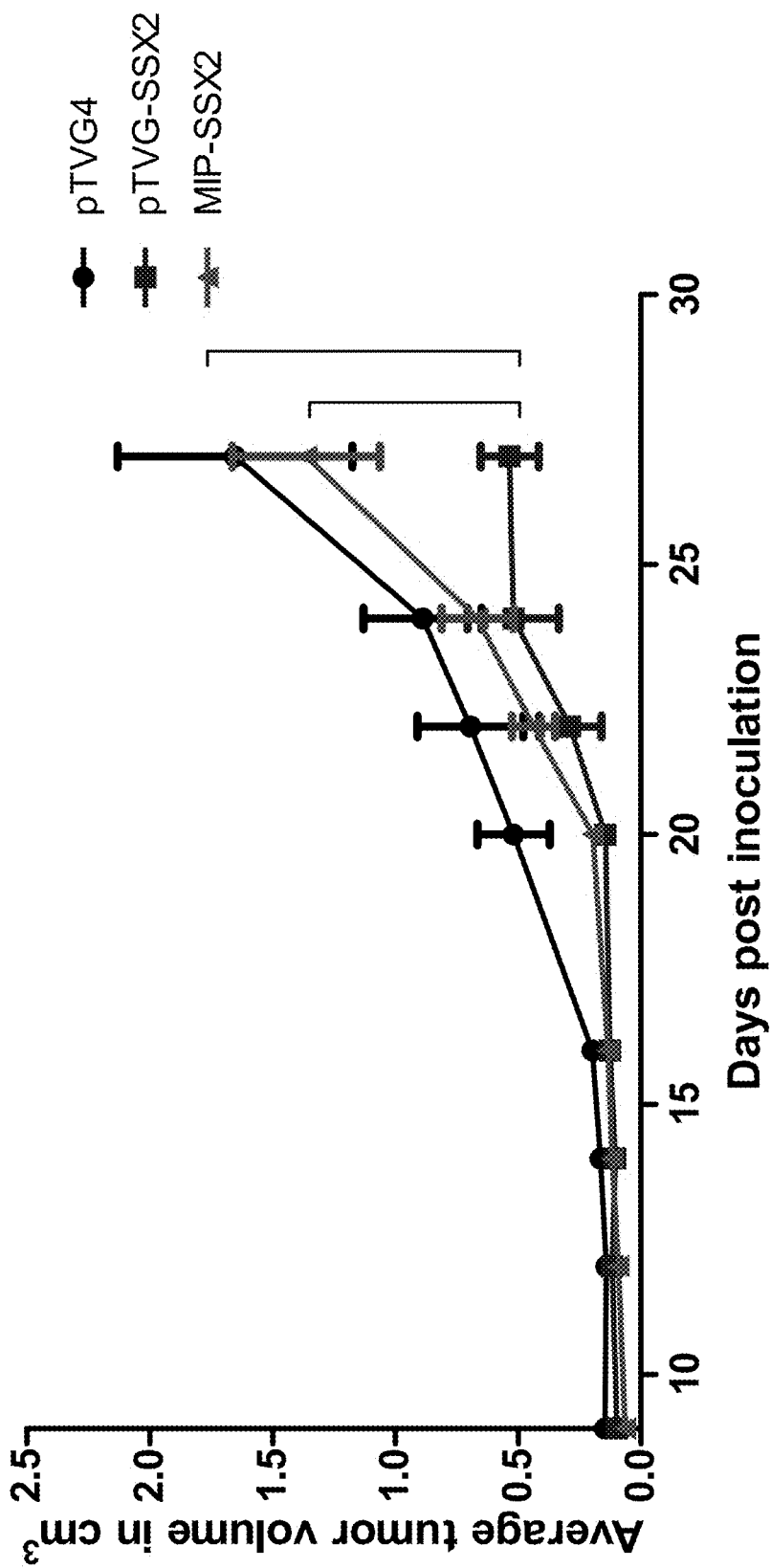

FIG. 9B is a graph showing tumor growth as a function of time for HLA-A2 expressing mice that were implanted subcutaneously with A2/Sarcoma cells and immunized with plasmid DNA encoding SSX2 (pTVG-SSX2), mini-intronic plasmids encoding SSX2 (MIP-SSX2), or vector control (pTVG4). Tumor growth was measured by volumetric measurements 3 times a week. Surprisingly, mice immunized with MIP-SSX2 exhibited greater tumor growth than mice immunized with pTVG-SSX2.

Figure 10A:
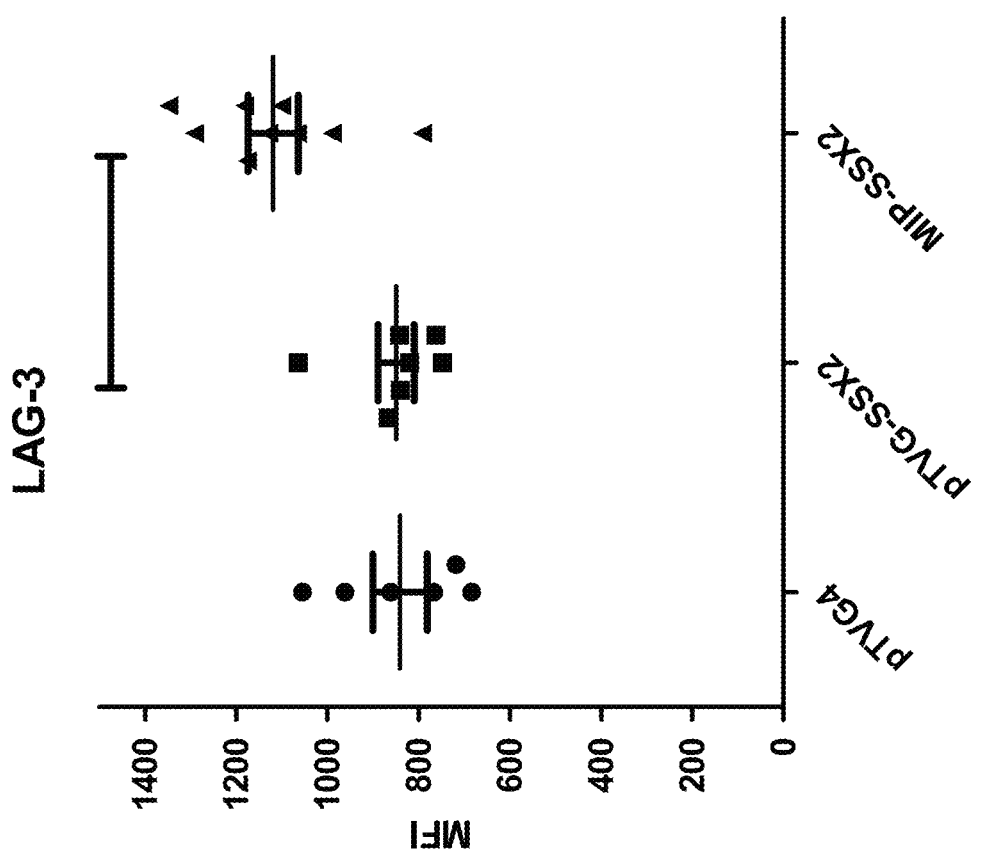

FIG. 10A shows LAG-3, expression data for tumor infiltrating lymphocytes (TILs) obtained from mice immunized with plasmid DNA encoding SSX2 (pTVG-SSX2), mini-intronic plasmids encoding SSX2 (MIP-SSX2), or vector control (pTVG4). TILs from each animal were obtained by enzymatic digestion and analyzed by flow cytometry. MFI is mean fluorescence intensity. As shown in FIG. 10A, CD8 TILs from MIP treated animals displayed elevated levels of LAG-3, a cell surface immune checkpoint protein associated with immunotolerance and anergy. Other regulatory markers on CD8 TILs and CD4 TILS (data not shown) remained unchanged. This data shows that increased LAG-3 expression in mice immunized with MIP DNA vaccines likely explains the tumor growth results shown in FIGS. 9A and 9B. Co-administration of a LAG-3 blocking agent would likely lead to reduced tumor growth in MIP-immunized animals.

Figure 10B:
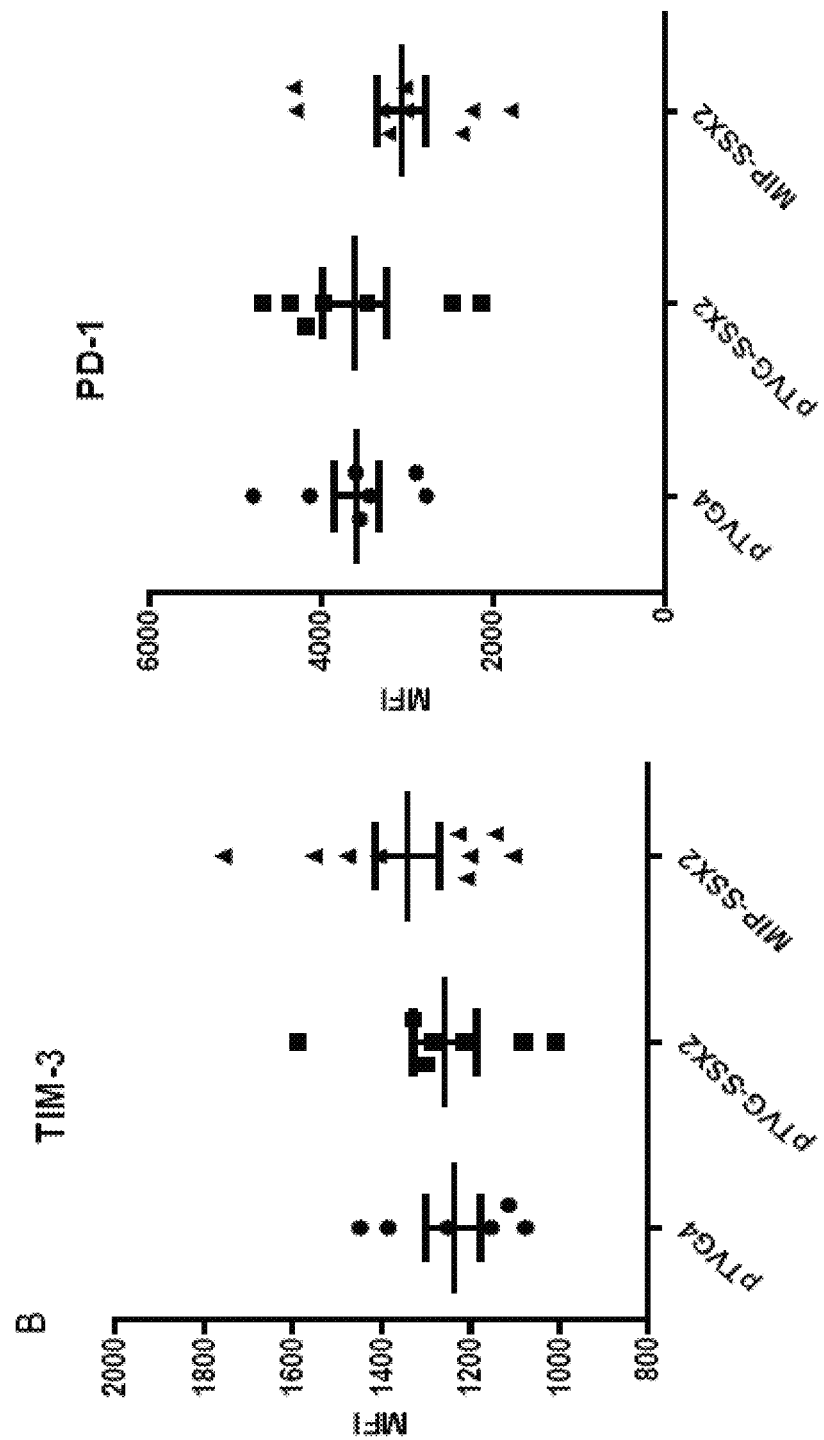

FIG. 10B demonstrates TIM-3 and PD-1 expression data for tumor infiltrating lymphocytes (TILs) obtained from mice immunized with plasmid DNA encoding SSX2 (pTVG-SSX2), mini-intronic plasmids encoding SSX2 (MIP-SSX2), or vector control (pTVG4). TILs from each animal were obtained by enzymatic digestion and analyzed by flow cytometry. MFI is mean fluorescence intensity. Other regulatory markers on CD8 TILs and CD4 TILS (data not shown) remained unchanged.

Figure 11:
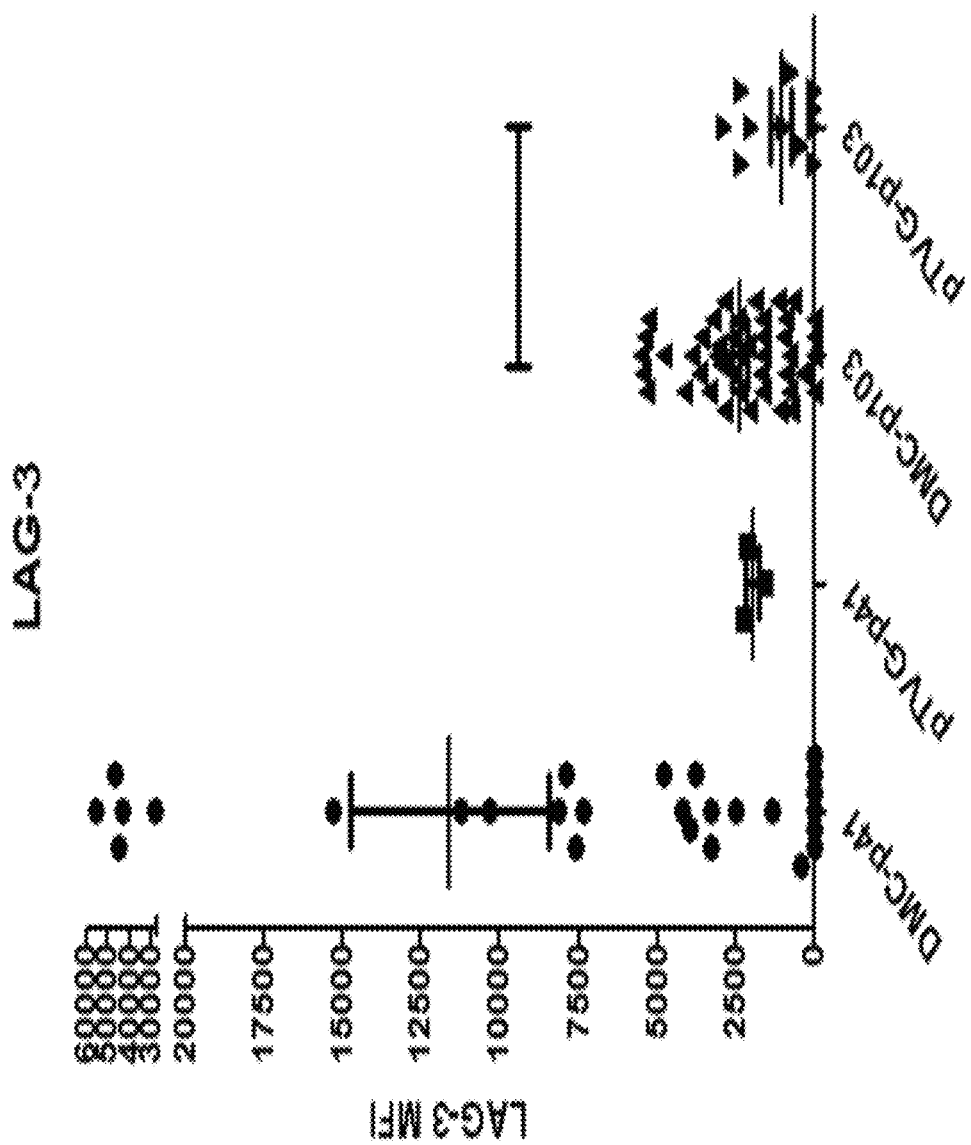

FIG. 11 shows LAG-3 expression data obtained using flow cytometry for splenocytes from naïve animals previously immunized with sustained expression vector DMC-SSX2. Splenocytes from previously immunized naïve animals were stained with p41 and p103 tetramers (to identify SSX2 antigen-specific T cells) and analyzed for levels of LAG3. P41 and p103 specific cells from non-tumor-bearing mice that were immunized with DMC-SSX2 had elevated levels of LAG3, in comparison to mice that were immunized with conventional plasmid vector pTVG-SSX2. This data establishes that the elevated levels of LAG-3 expression exhibited by TILs from MIP-SSX2 immunized animals (see FIG. 10) were a function of the type of vector used, rather than being tumor-dependent.

Figure 12:
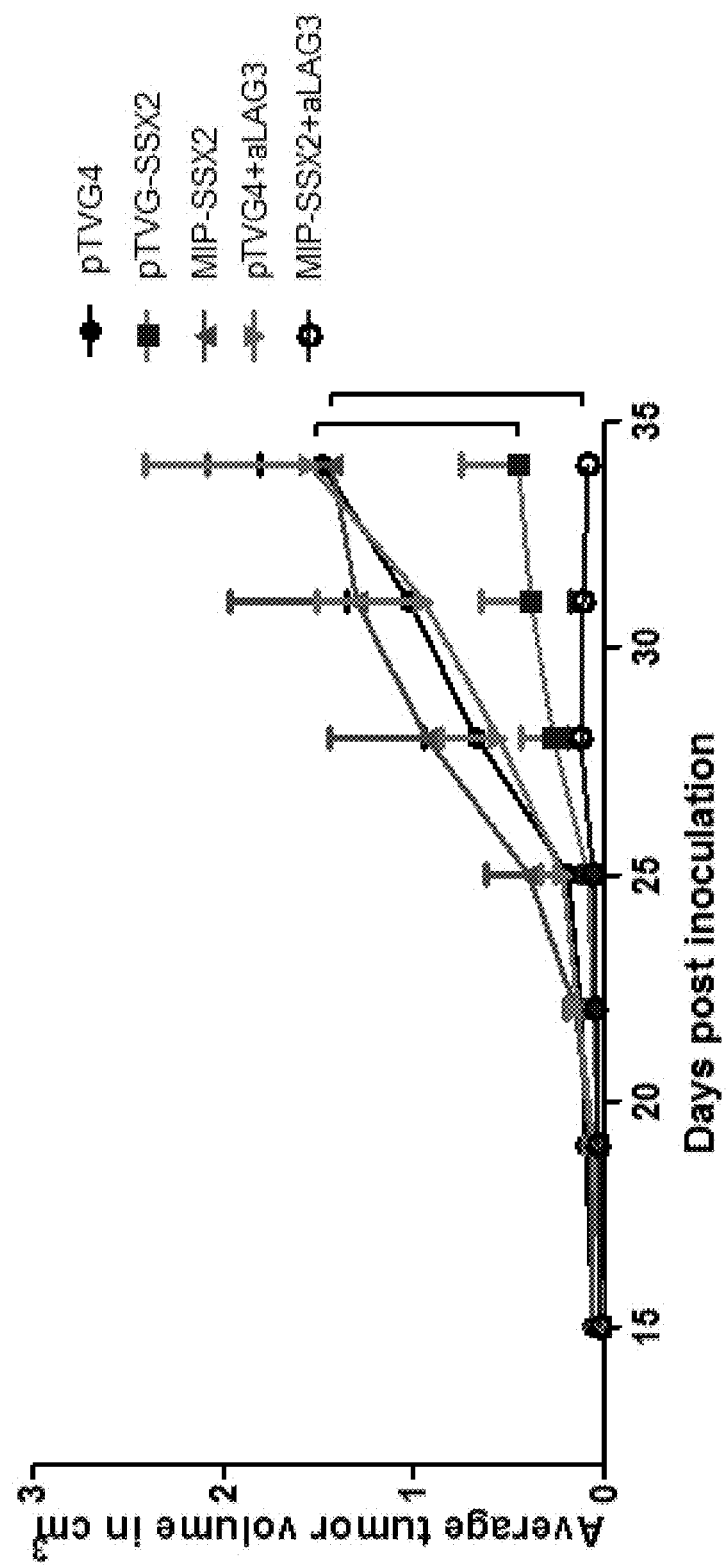

FIG. 12 is a graph showing tumor growth as a function of time for HLA-A2 (average of n=6 per group) expressing mice that were implanted subcutaneously with A2/Sarcoma cells and immunized bi-weekly with plasmid DNA encoding SSX2 (pTVG-SSX2), mini-intronic plasmids encoding SSX2 (MIP-SSX2), or vector control (pTVG4) alone or in combination with 200 µg of a monoclonal antibody against murine LAG3 (clone C9B7W, BioXCell) administered 24 h and 72 h after vaccination. Tumor growth was measured by volumetric measurements 3 times a week.

Figure 13:
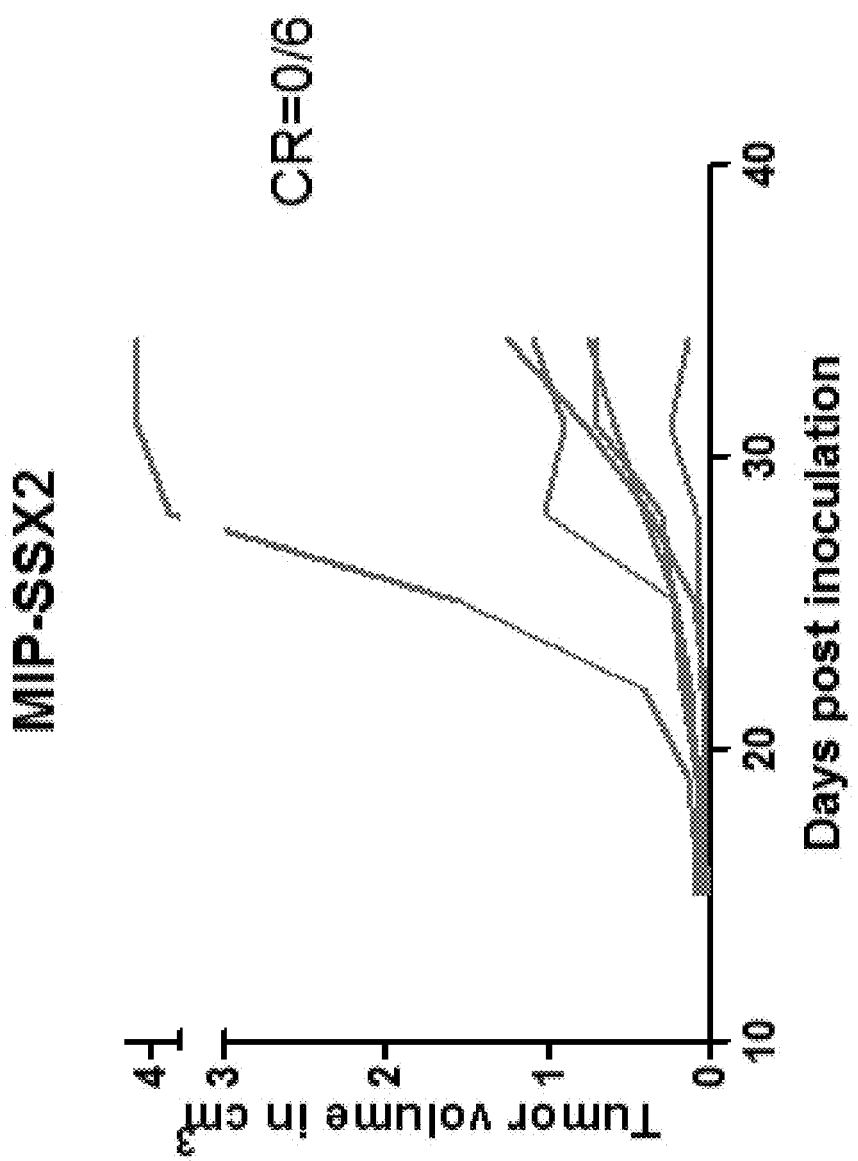

FIG. 13 is a graph that shows individual tumor growth curves for each animal treated with MIP-SSX2 alone. CR=complete response.

Figure 14:
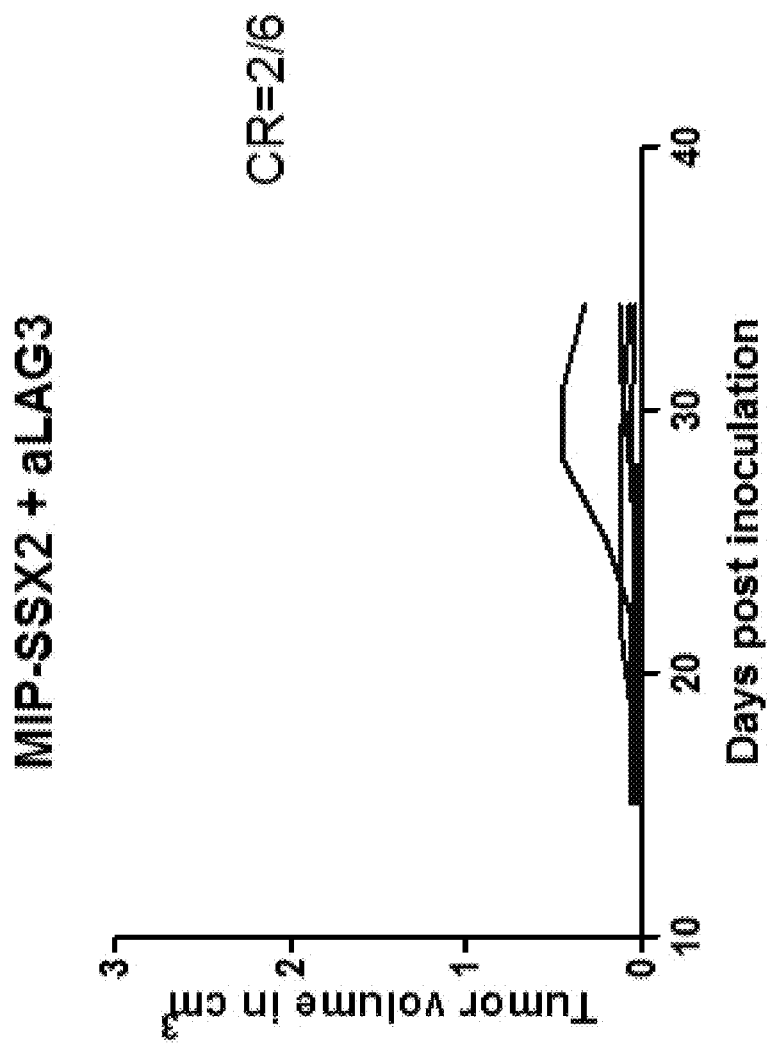

FIG. 14 shows individual tumor growth curves for each animal treated with MIP-SSX2 in combination with LAG3 blockade. CR=Complete response.

Figure 15:
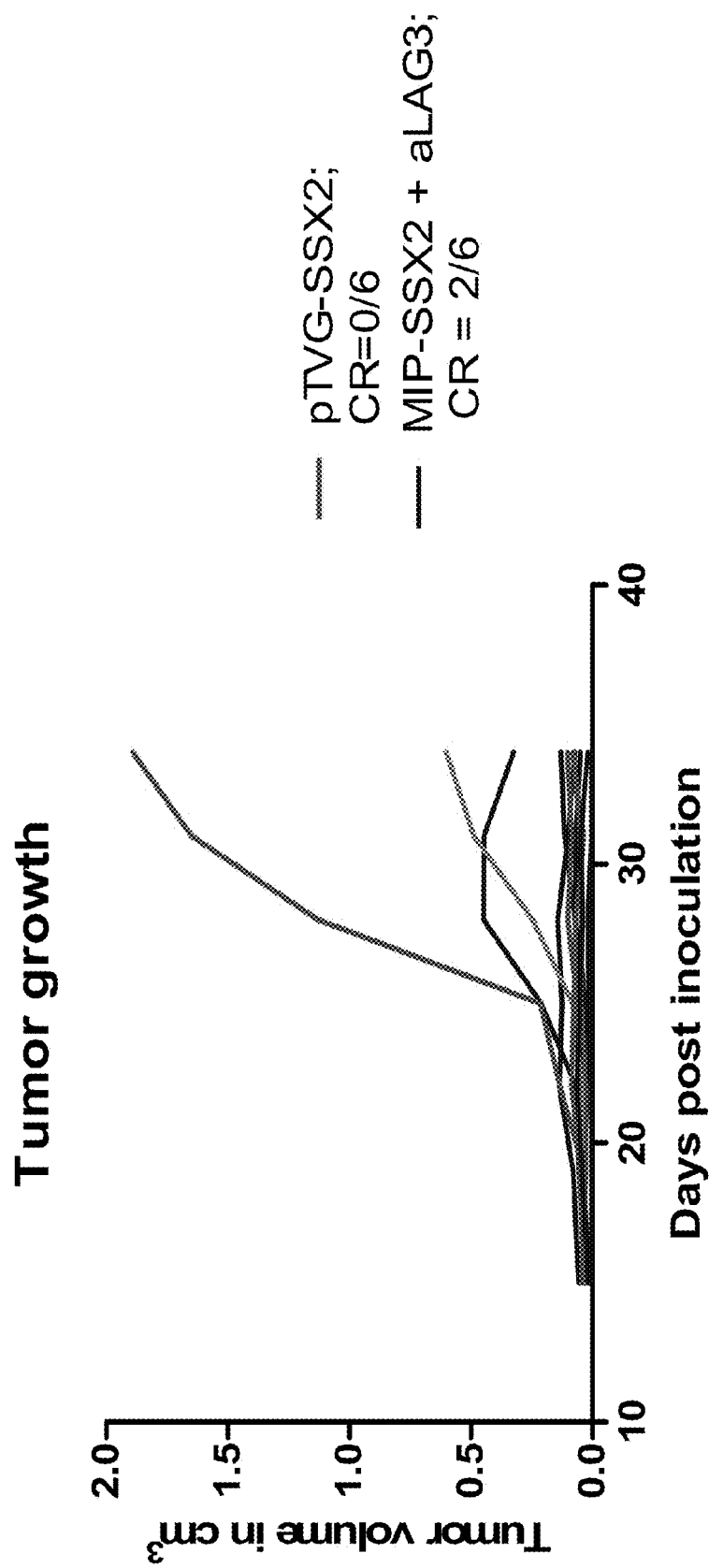

FIG. 15 shows individual tumor growth curves of groups treated with pTVG-SSX2 alone (red) or the MIP-SSX2+ anti-LAG-3 antibody (aLAG3) combination (blue).

Figure 16:
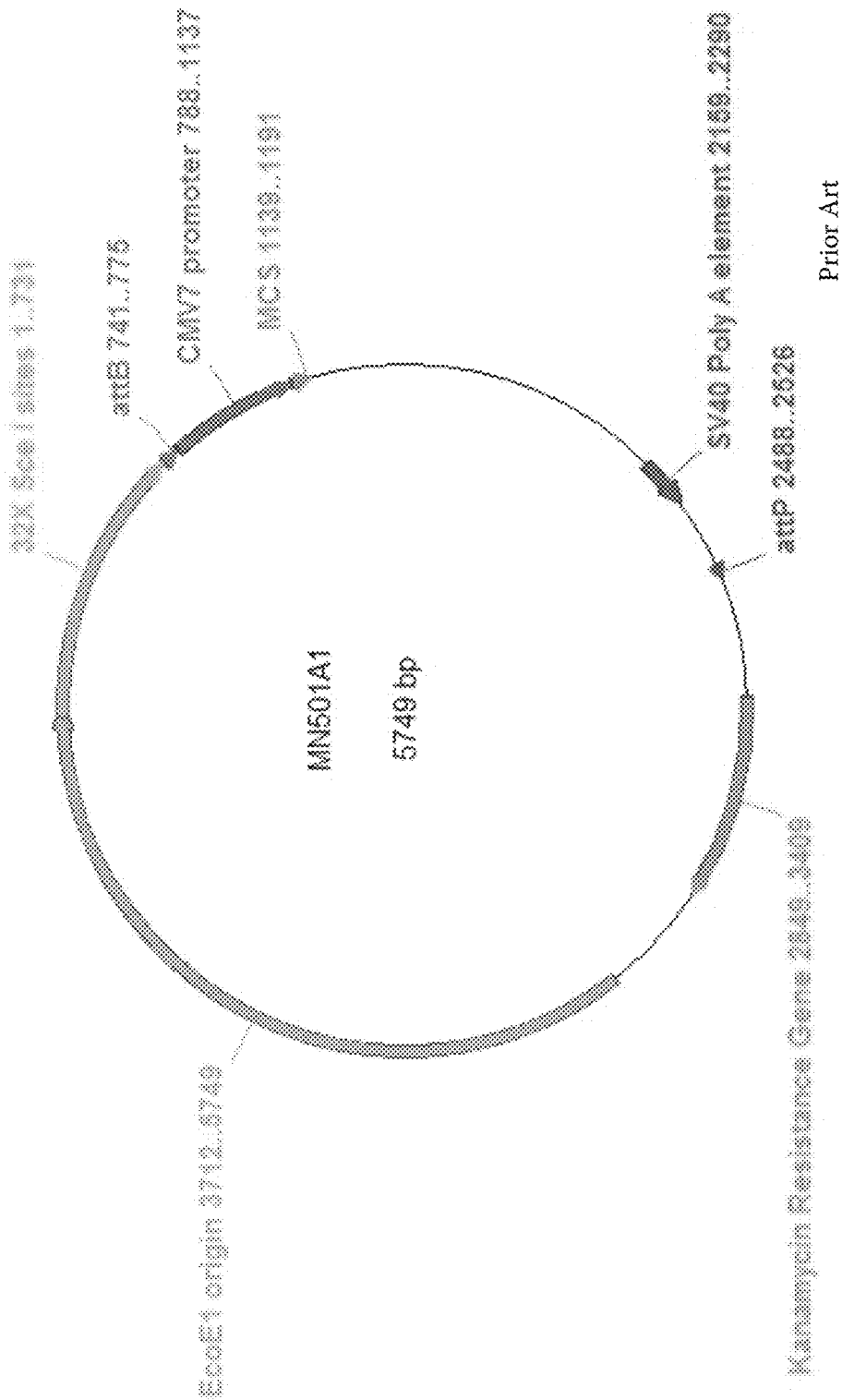

FIG. 16 is a plasmid map for the commercially available MN501A-1 parent vector.

Figure 17:
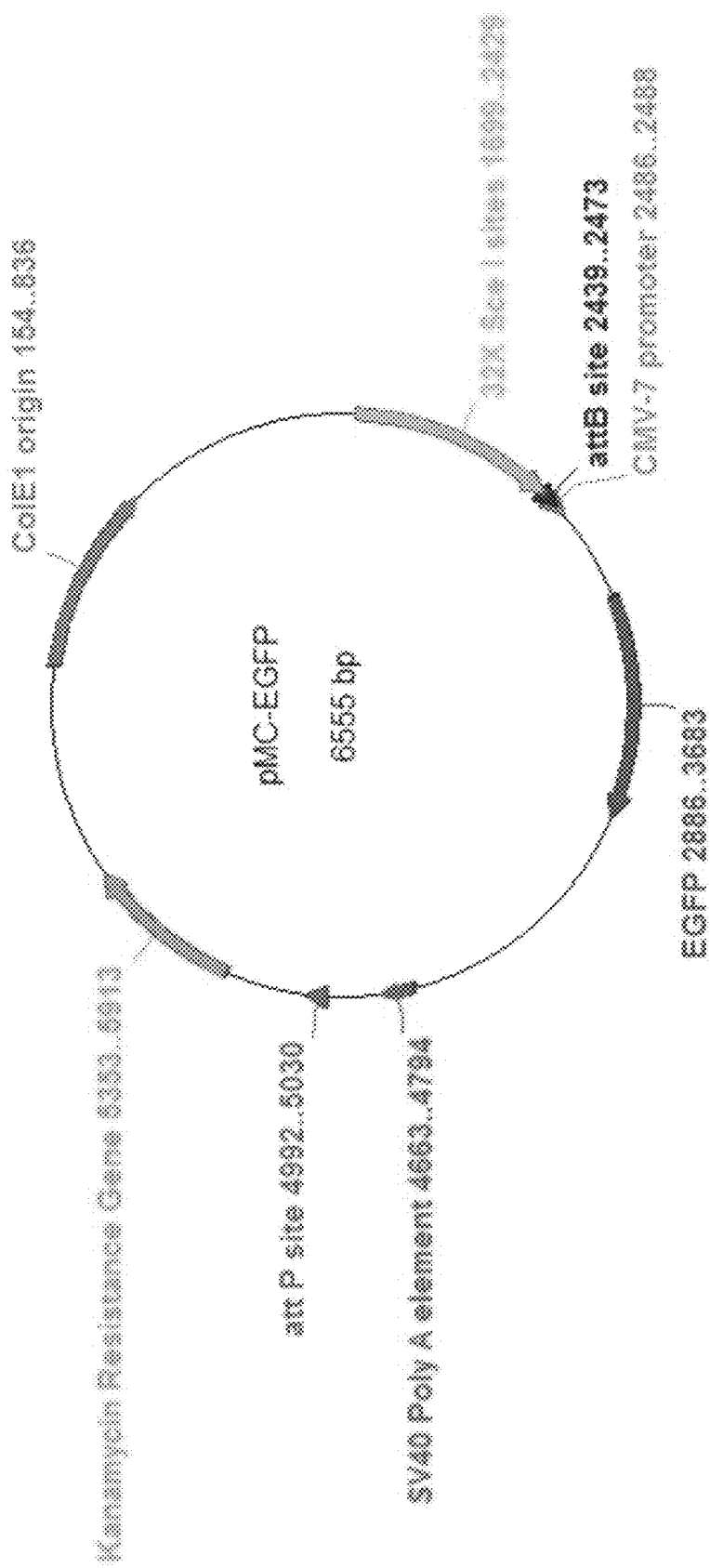
Figure 18:
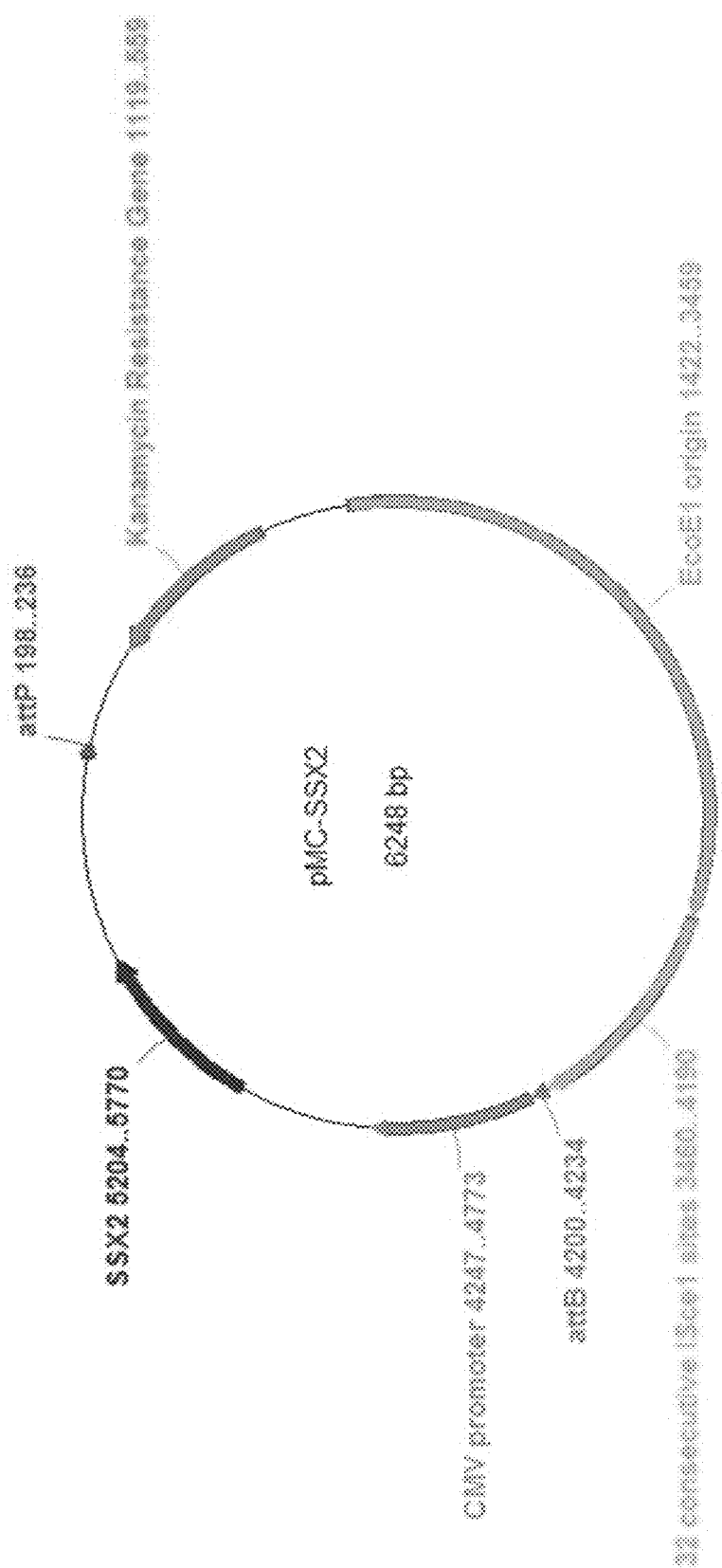
Figure 19:
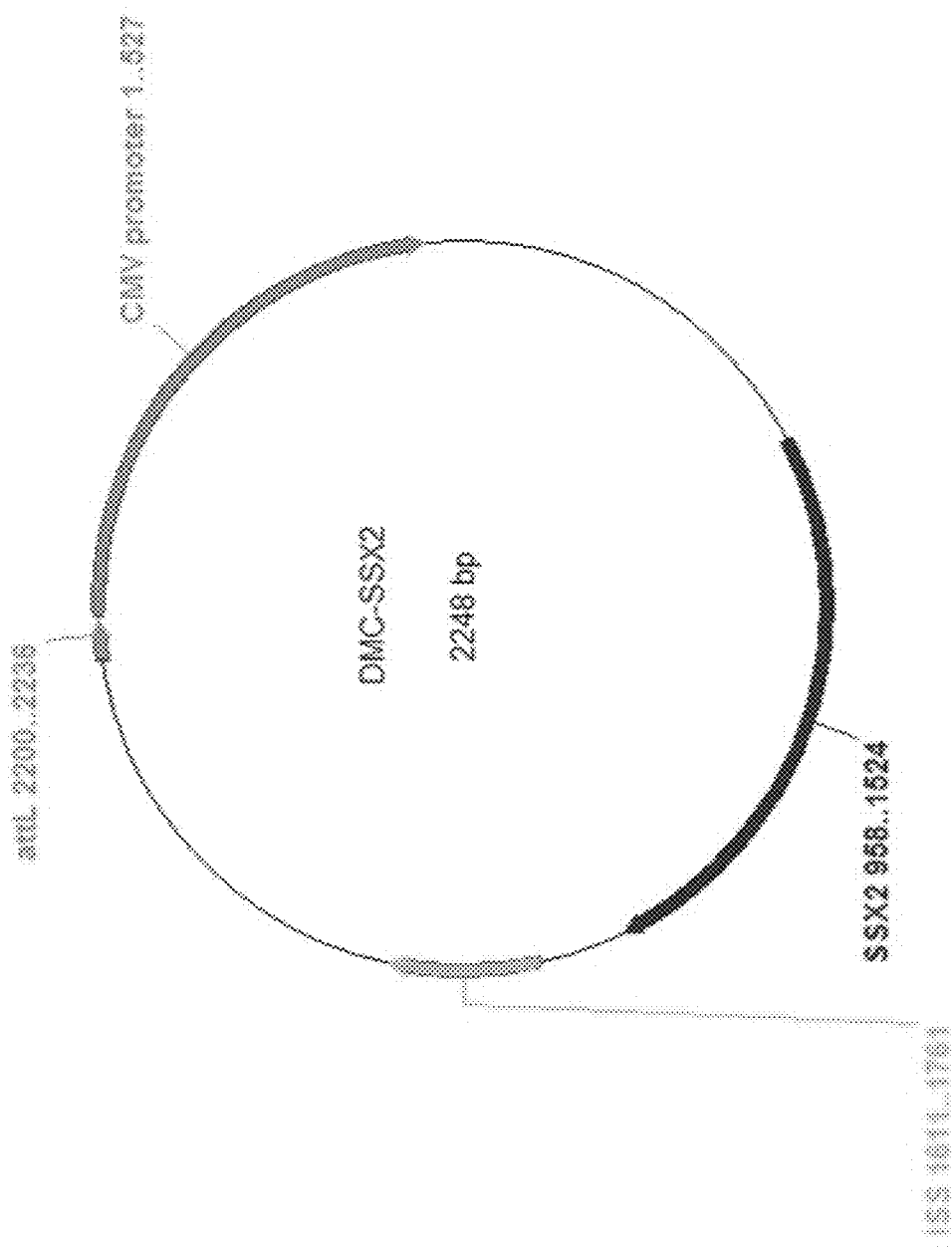
Figure 20:
Figure 21:
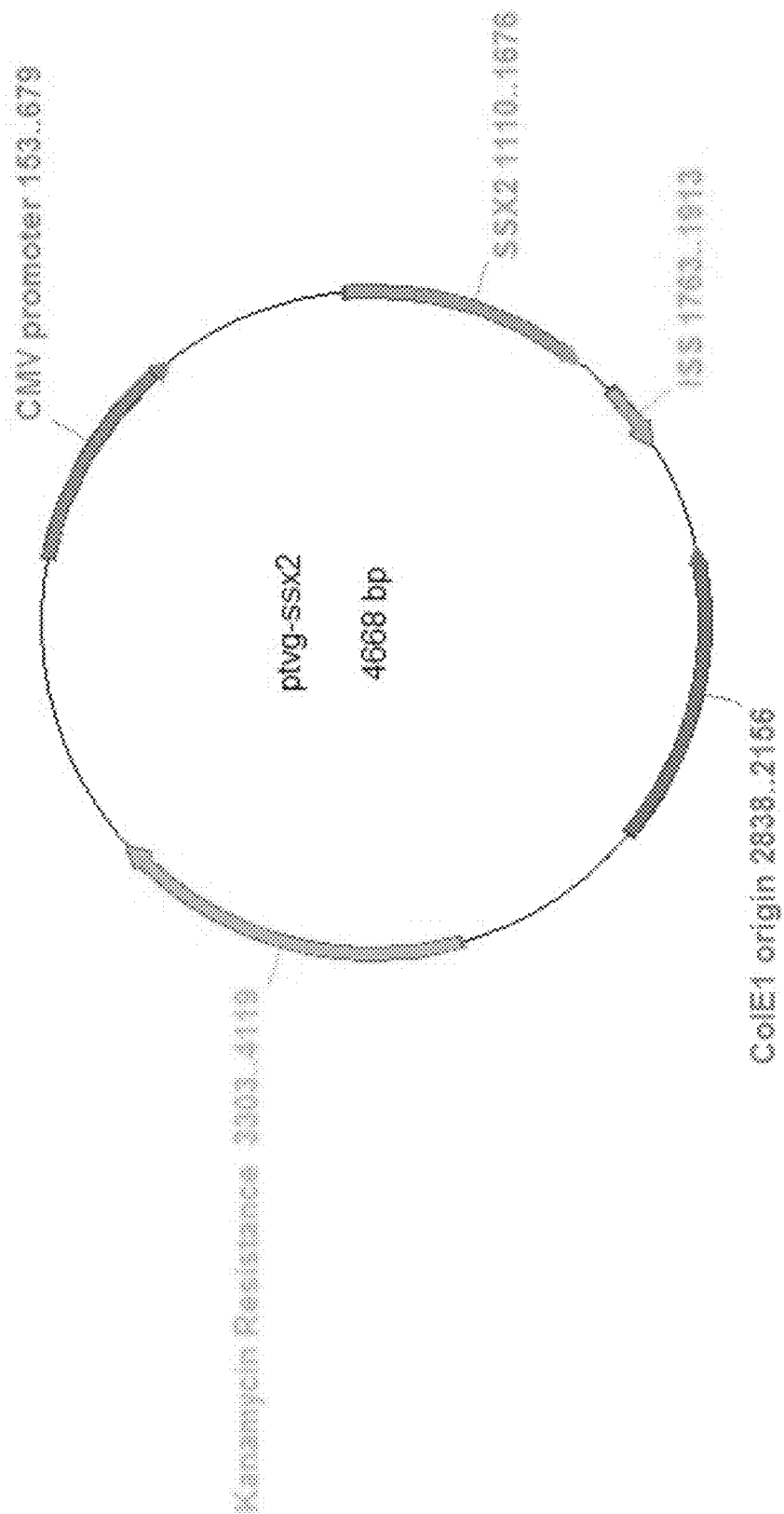

FIG. 17 is a plasmid map for the pMC-GFP vector.
FIG. 18 is a plasmid map for the pMC-SSX2 vector.
FIG. 19 is a plasmid map for the DMC-SSX2 vector.
FIG. 20 is a plasmid map for the MIP-SSX2 vector.
FIG. 21 is a plasmid map for the TVG-SSX2 vector.

DETAILED DESCRIPTION

This disclosure provides compositions and methods related to the use of DNA vaccines delivered using mini-intronic plasmids in combination with administering a LAG-3 pathway blocking agent. This specific combination unexpectedly and synergistically improves the efficacy of such vaccines for the treatment of a number of disorders. Although the model systems demonstrating the disclosed methods are directed to prostate cancer treatment using a plasmid coding for the cancer-testis antigen SSX-2, the disclosed methods are applicable to any disorder that can be prevented or treated using the disclosed compositions and methods, including, without limitation, every condition for which DNA vaccines have been created and successfully evaluated in preclinical studies (see, e.g., Liu et al. (2011), DNA vaccines: an historical perspective and view to the future, Immunol Rev. 239 (1): 62-84, which is incorporated by reference herein in its entirety).

Such conditions include viral infections, such as HIV, Influenza, Rabies, Hepatitis B and C, Ebola, Herpes simplex, Papilloma, CMV, Rotavirus, Measles, LCMV, St. Louis encephalitis, and West Nile virus; bacterial infections, such as *B. Burgdorferi, C. Tetani, M Tb.*, and *S. Typhi*; parasitic infections, such as malaria, mycoplasma, leishmania, Toxo. Gondii, Taenia ovis, and schistosoma; cancers (including but not limited to breast, colon, prostate, myeloma, renal cell cancer, bladder cancer, melanoma, brain tumors, lung cancers, E7-induced cancer, lymphomas, and sarcomas); allergic conditions, such as house dust mite, experimental airway hyperresponsiveness (Asthma), and peanut allergy; and autoimmune diseases, such as diabetes, and EAE (Multiple sclerosis model).

In some embodiments, the encoded antigen is synovial sarcoma X breakpoint 2 (SSX2), androgen receptor ligand-binding domain (AR LBD), prostate-specific antigen (PSA), human epidermal growth factor receptor 2 (HER-2/neu), or prostatic acid phosphatase (PAP).

In some embodiments, the polynucleotide of interest encodes a fragment or epitope of the antigen. For example, in some embodiments, HLA-A2 restricted epitopes of the antigen may be used. Epitopes for use in the invention are known in the art. For example, suitable HLA-A2 restricted epitopes for SSX2, AR LBD, and PAP can be found in, for example, but not limited to, Olson B M, Frye T P, Johnson L D, Fong L, Knutson K L, Disis M L, and McNeel D G. (2010) "HLA-A2-restricted T-cell epitopes specific for prostatic acid phosphatase." *Cancer Immunol. Immunother.* 59:943-953. (PMID 20140431, PMCID: PMC3038205); Olson B M and McNeel D G. (2011) "CD8+ T cells specific for the androgen receptor are common in patients with prostate cancer and are able to lyse prostate tumor cells." *Cancer Immunol. Immunoth.* 60:781-792. (PMID: 21350948, PMCID: PMC3319721); and Smith H A and McNeel D G. (2011) "Vaccines targeting the cancer-testis antigen SSX-2 elicit HLA-A2 epitope-specific cytolytic T cells." *J. Immunotherapy* 34:569-580. (PMID:21904219, PMCID: PMC3175298), all of which are incorporated by reference in their entirety. In some embodiments, the selectable marker is an antibiotic resistance gene.

In some embodiments, the compositions and methods are used to reduce the number of cells of the target cell types in a subject in need of such treatment. When the target cell type is a cancer cell, suitable subjects in need of such treatment include subjects suffering from, recovering from or having cancer, for example, but not limited to, subjects with prostate cancer, malignant melanoma, colon cancer, liver cancer, lung cancer, ovarian cancer, renal cancer, pancreatic cancer, or breast cancer or the like.

MIP vectors have been used in some gene therapy studies, but no one has previously suggested using this technology together with a LAG-3 blocking agent to increase the efficacy of the DNA vaccine, as suggested by the inventors' findings disclosed herein. Specific aspects of the disclosed methods and compositions are described in further detail below.

A. Mini-Intronic Plasmid Vectors (MIPs)

In the present disclosure, the DNA vector encoding the antigen of interest is in the form of a mini-intronic plasmid (MIP). A conventional plasmid is a circular DNA vector that includes an expression cassette and a separate plasmid backbone. An "expression cassette" is a nucleic acid construct capable of directing the expression of a RNA transcript coding for a polypeptide of interest. An expression cassette generally includes a 5' promoter region that is recognized by the host organism and that is operably linked to the coding sequence, i.e. the DNA sequence encoding for the RNA transcript that is translated to produce the polypeptide of interest. The promoter region is generally an untranslated sequence located upstream (5') to the start codon of the structural gene (generally within about 100 to 1000 bases) that modulates the transcription and translation of the particular nucleic acid sequence to which it is operably linked. An expression cassette may also contain sequences necessary for the termination of transcription and for stabilizing the resulting mRNA, such as regions transcribed as polyadenylated fragments in the untranslated portion of the mRNA encoding for the polypeptide of interest.

The "plasmid backbone" is the region of a conventional plasmid outside of the expression cassette that includes an origin of replication and a selectable marker, as well as bacterial sequences that flank these elements. An "origin of replication" is the particular sequence at which plasmid replication is initiated. An origin of replication is required for the episomal (i.e. extragenomic) propagation of the plasmid in a host cell. A "selectable marker" is a coding sequence that allows for selective retention of cells comprising a nucleic acid of interest (e.g. a plasmid) during culturing and propagation in the host cells. Non-limiting examples of selectable markers include those genes useful in antibiotic resistance systems, e.g. ampicillin, kanamycin, neomycin; and those genes useful in RNA-based selection schemes, e.g. antisense regulators (e.g. RNA-OUT) that inhibit the translation of a gene (SacB) transcribed from the host chromosome that would otherwise promote cell death.

The MIP vector used in the disclosed methods and compositions includes a MIP intron containing the origin of replication and the selectable marker that are commonly included in the plasmid backbone of a conventional plasmid (or other selectable markers, such as RNA-out). However, instead of being located in a region of the plasmid that is separate from the expression cassette, as in a conventional plasmid, the MIP intron containing the plasmid backbone elements is inserted within the expression cassette itself. Thus, unlike a conventional plasmid, a MIP vector does not include a plasmid backbone region separate from the expression cassette.

In some embodiments, the MIP intron is operably linked to the same promoter that mediates the expression of the polypeptide of interest by the MIP vector. Thus, the MIP intron is an integral part of the expression cassette. In such instances, the MIP intron may be located in any configuration relative to the sequence encoding for the polypeptide of interest (the "coding sequence"). In some embodiments, the MIP intron may be located upstream, or 5', of the coding sequence, i.e. between the promoter and the initiation codon for the coding sequence. In other embodiments, the MIP intron may be located within the coding sequence, i.e. flanked by two exons of the coding sequence. In other embodiments, the MIP intron may be located downstream of the coding sequence. For example, if the coding sequence does not include a termination sequence, the MIP intron may be placed downstream of the coding sequence and upstream of an exogenous termination, e.g. a polyadenylation, sequence.

The MIP vector is substantially free of any bacterial plasmid backbone sequences other than those sequences that are included within the MIP intron. Specifically, the MIP vector is devoid of any bacterial origin of replication or selectable marker located outside of the MIP intron. Furthermore, the MIP vector is generally restricted to an extragenic spacer length of 500 nucleotides or less.

Mini-intronic plasmid vectors may be prepared in any of a number of ways using known techniques, and are further described in U.S. Patent Publication No. 2013/0210897, which is incorporated by reference herein in its entirety.

B. LAG-3 Blocking Agents

In the present disclosure, in some embodiments, a LAG-3 blocking agent is co-administered with a MIP-delivered DNA vaccine. As used herein, the terms "co-administer" or "co-administration" refer to administering two or more agents to the same subject during a treatment period. The two or more agents may be encompassed in a single formulation and thus be administered simultaneously. Alternatively, the two or more agents may be in separate physical formulations and administered separately, either sequentially or simultaneously to the subject. The term "administered simultaneously" or "simultaneous administration" means that the administration of the first agent and that of a second agent overlap in time with each other. The term "administered sequentially" or "sequential administration" means that the administration of the first agent and of a second agent do not overlap in time with each other. In some embodiments, the MIP-delivered vaccine is administered as the first agent and the LAG-3 blocking agent is administered as the second agent. In some embodiments, the first agent and second agent are administered sequentially. In some embodiments, the first and second agent are administered in close proximity of time. In some embodiments, the first agent and second agent are administered after a given period of time. In some embodiments, the given period of time may be a sufficient time after eliciting a LAG-3 regulated response by the MIP vaccine administration. Administration can be repeated in any given combination. In some embodiments, a first agent is administered in a first court of treatment followed by administration of the second agent in a second course of treatment. In some instances, the first course of treatment and the second course of treatment may overlap.

The LAG-3 blocking agent can be any composition or compound capable of blocking the LAG-3 immune checkpoint pathway. In some embodiments, the LAG-3 blocking agent is an antibody capable of binding the LAG-3 immune checkpoint protein, thus modulating LAG-3's interaction with its ligand. Such antibodies are disclosed in, e.g., U.S. Patent Publication Nos. 2011/0150892 and US 2014/0093511, each of which is incorporated by reference in its entirety.

In some embodiments, the LAG-3 immune checkpoint protein pathway blocking agent is s a blocking agent that binds or inhibits a protein or ligand required in the LAG-3 pathway. A LAG-3 blocking agent that binds or inhibits a protein or ligand of the LAG-3 pathway includes any inhibitor or antibody that results in a decrease or reduced activation of the LAG-3 pathway. Decreased or reduced activation of the LAG-3 pathway may result in reduced expression or reduced upregulation of LAG-3 expression in CD8+ cells. In the present disclosure, a LAG-3 pathway blocking agent is co-administered or administered sequentially with a MIP-delivered DNA vaccine to synergistically enhance the CD8+ response to the tumor antigen. In some embodiments, the LAG-3 immune checkpoint protein pathway blocking agent is an inhibitor of a ligand or binding partner of LAG-3. In some embodiments, the inhibitor may be a protein that binds the ligand or binding partner of LAG-3 and inhibits interaction of the ligand or binding partner with LAG-3. The ligand or binding partner may be Galectin-3 or MHC-II.

In some embodiments, the LAG-3 immune checkpoint protein pathway blocking agent is an inhibitor of or an antibody that binds Galectin-3 or MHC-II.

In other words, the LAG-3 pathway blocking agent can be any composition or compound capable of blocking a protein or ligand involved in the LAG-3 immune checkpoint pathway that will result in the reduction or downregulation of LAG-3. In some embodiments, the LAG-3 pathway blocking agent is an antibody or inhibitor capable of inhibiting the binding of a ligand or binding partner to LAG-3 immune checkpoint protein, thus modulating the ligand's or binding partner's interaction with LAG-3 and down-regulating the expression of LAG-3. In some embodiments, the LAG-3 ligand includes, but is not limited to, Galectin-3 or MHC-II. Discussion of the role of Galectin-3 as a LAG-3 ligand is disclosed in Kouo et al. "Galectin-3 Shapes Antitumor Immune Responses by Suppressing CD8+ T Cells via LAG-3 and Inhibiting Expansion of Plasmacytoid Dendritic Cells" Cancer Immun. Res.; 3(4), April 2015 412-423, which is incorporated by reference in its entirety.

In some embodiments, the LAG-3 pathway blocking agent is an inhibitor of or an antibody that binds Galectin-3. Suitable inhibitors of Galectin-3 include small molecule inhibitors known in the art. Not to be bound by any theory, small molecule inhibitors of Galectin-3 may bind Galectin-3 molecule with artificial ligands of higher binding affinity than the natural sugar residue that binds it N-acetylglucosamine. Some suitable inhibitors of Galectin-3, are know in the art and include, but are not limited to, inhibitors described in Yu, L., Ruifrok, W. P. T., Meissner, M., Bos, E. M., Goor, H. van, Sanjabi, B., Harst, P. van der, Pitt, B., Goldstein, I. J., Koerts, J. A., et al. (2013). Genetic and Pharmacological Inhibition of Galectin-3 Prevents Cardiac Remodeling by Interfering With Myocardial Fibrogenesis. Circ Heart Fail 6, 107-117; Glinsky, V. V., Kiriakova, G., Glinskii, O. V., Mossine, V. V., Mawhinney, T. P., Turk, J. R., Glinskii, A. B., Huxley, V. H., Price, J. E., and Glinsky, G. V. (2009). Synthetic Galectin-3 Inhibitor Increases Metastatic Cancer Cell Sensitivity to Taxol-Induced Apoptosis In Vitro and In Vivo. Neoplasia 11, 901-909; and Blanchard, H., Yu, X., Collins, P. M., and Bum-Erdene, K. (2014). Galectin-3 inhibitors: a patent review (2008-present). Expert Opin Ther Pat 24, 1053-1065, the contents of which are incorporated by reference in their entireties. For example, a suitable inhibitor includes, for example, n-acetyl-d-glucosamine (GlcNAc).

In other embodiments, the LAG-3 pathway blocking agent is an antibody that binds to MHC-II. In other embodiments, the LAG-3 pathway blocking agent is an inhibitor that blocks MHC-II binding or activation of the LAG-3 pathway.

The invention will be more fully understood upon consideration of the following non-limiting examples. Each publication, patent, and patent publication cited in this disclosure is incorporated in reference herein in its entirety.

Example 1

Minicircle Vectors and Mini-Intronic Plasmid Vectors Facilitate Sustained Antigen Expression and Production of Antigen-Specific T Cells In this Example, we demonstrate that using minicircle vectors or mini-intronic plasmid vectors as model DNA vaccines promotes more sustained antigen expression in the cells taking up the vectors, as compared to using conventional plasmid vectors. Furthermore, we demonstrate that using minicircle vectors or mini-intronic plasmid vectors as model DNA vaccines elicits a stronger T cell-mediated immune response, as compared to conventional plasmid vectors.

A. DNA Vectors Used.

Conventional Plasmid Vectors.

In the immunization experiments reported below, the conventional plasmid vector pTVG4 was used as a vector control. The pTVG4 is the parental vector that does not contain an antigen. The construction of pTVG4 is described in U.S. Pat. No. 7,179,797, which is incorporated by reference herein in its entirety. The plasmid vector containing the SSX2 antigen, pTVG-SSX2 is described in Smith H A, McNeel D G. Vaccines targeting the cancer-testis antigen SSX-2 elicit HLA-A2 epitope-specific cytolytic T cells. J Immunother. 2011; 34:569-80, which is incorporated by reference in its entirety.

In the GFP-based expression experiments reported below, GFP functions as a reporter gene for which expression can be directly assessed, by virtue of the fluorescence of the gene product. The DNA coding sequence for green fluorescence protein (GFP) was cloned into a commercially available pMC parent vector: pMC.CMV-MCS-SV40 polyA (System Biosciences, catalog No.: MN501A-1; see FIG. 16) to produce a conventional plasmid coding for GFP (pMC-GFP; see FIG. 17). For the antigen expression and immunization experiments reported below, the DNA coding sequence for synovial sarcoma X breakpoint 2 antigen (SSX2) was cloned into the pTVG4 vector to produce conventional plasmid coding for SSX2 (pTVG-SSX2; see FIG. 18).

DNA Minicircle Vectors (DMCs).

DNA minicircle vectors devoid of the plasmid backbone of the pMC-GFP vectors (DMC-GFP) were prepared by site-specific recombination of the 3' and 5' ends of the pMC-GFP vector expression cassette within the *E. coli* host, and subsequent excision of the plasmid backbone. DNA Minicircle vectors encoding for SSX2 (DMC-SSX2; see FIG. 16) were also constructed from the conventional plasmids by site-specific recombination and excision. General methods for constructing minicircle DNA vectors from conventional plasmid vectors are described in detail in Dietz, W. M., Skinner, N. E. B., Hamilton, S. E., Jund, M. D., Heitfeld, S. M., Litterman, A. J., Hwu, P., Chen, Z., Salazar, A. M., Ohlfest, J. R., Blazar, B. R., Pennell, C. A., and Osborn, M. J. (2013), Minicircle DNA is superior to plasmid DNA in eliciting antigen-specific CD8+ T-cell responses, *Mol Ther* 21: 1526-1535, which is incorporated by reference herein in its entirety.

Figure 1:
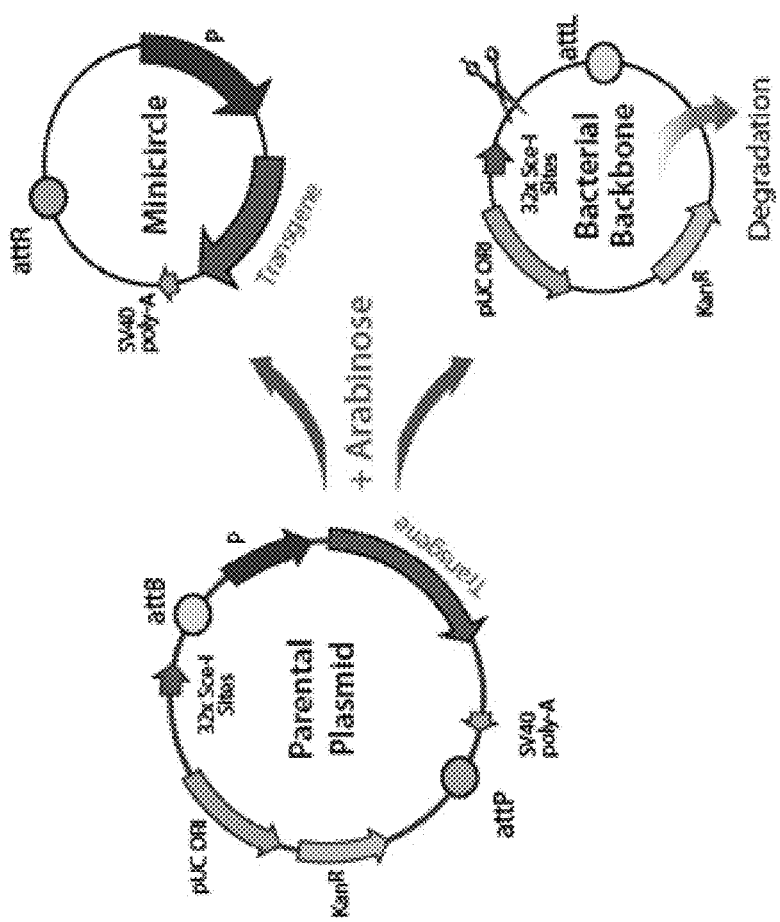
FIG. 1 is a schematic diagram illustrating the construction of DNA minicircle vectors (MCs) designed to be taken up by cells and to express within the cells a nucleic acid sequence coding for a polypeptide of interest (i.e., a transgene). The MC is constructed from conventional plasmids containing two primary regions: (1) an expression cassette, which includes the promoter (P), the DNA sequence coding for the polypeptide of interest (the transgene), and a transcription terminating poly-A sequence (SV40 poly-A)); and (2) a plasmid backbone, which includes the origin of replication (pUC ORI) and the antibiotic resistance marker (KanR) (see left panel). The conventional plasmid, which is grown and replicated in *Escherichia coli* using standard methods, undergoes site-specific recombination (at attP and attB) and excision within the host bacteria, resulting in a minicircle that includes only the expression cassette (top right), and a leftover construct that includes the plasmid backbone, which is subsequently degraded (bottom right). The DNA MC vectors are then isolated from the host bacteria. Note that the DMC-SSX2 (derived from pMC-SSX2; see FIG. 18) and MIP-SSX2 (derived from cloning an intron into DMC-SSX2) do not have an SV40 Poly A termination enhancer element. This was cloned in this fashion so as to execute a "true" controlled experiment when comparing to the pTVG-SSX2 (which does not have this particular vectoral element). pTVG-SSX2 can be found in Smith H A, McNeel D G.

FIG. 1 illustrates the construction of the specific DNA minicircle vectors (DMCs) used in this Example. Like conventional plasmids, DMCs are designed to be taken up by cells, where the polypeptide of interest (which in this Example is GFP or SSX2) is subsequently expressed within the cells. The conventional plasmid contains two primary regions. The first primary region is the expression cassette, which includes the promoter (P), the DNA sequence coding for the polypeptide of interest (the transgene, which in this Example is GFP or SSX2). Neither this vector nor the original pTVG4 vector includes a poly-A enhancer sequence. The second primary region is the plasmid backbone, which includes the origin of replication (pUC ORI) and the antibiotic resistance marker (KanR) (see FIG. 1, left panel).

The DNA minicircle vectors contain the entire expression cassette included in the conventional plasmids, but almost none of the plasmid backbone. The conventional plasmid, which is grown and replicated in an *Escherichia coli* strain genetically modified to express the PhiC31 recombinase that recognizes attB and ttP sites (for example, *E. coli* strain ZYCY10P3S2T available from SBI System Biosciences, Mountain View, Calif.) using standard methods, undergoes site-specific recombination between the phage attachment site (attP) downstream from the 3' end of the expression cassette (the end of the SV40 poly-A transcription termination sequence), and the bacterial attachment site (attB) upstream from the 5' end of the of the expression cassette (the beginning of the promoter region). Recombination between the attB and attP sites generates two separate circular constructs: a DNA minicircle that includes the expression cassette and a newly formed attR site marking the site of recombination (top right), and a leftover construct that includes most of the plasmid backbone and a newly formed attL site marking the site of recombination (bottom right), which is subsequently degraded. The DNA minicircle vectors are then isolated from the host bacteria using standard methods.

Mini-Intronic Plasmids (MIPs).

The mini-intronic plasmids used in these Examples were obtained by integrating the plasmid backbone, including the bacterial origin of replication and the selectable marker, within an engineered intron inserted within a non-coding exon within the expression cassette. Specifically, for the MIPs encoding the SSX2 antigen that were used in these Examples (MIP-SSX2; see FIG. 20), the MIP intron is inserted within the expression cassette upstream of the region encoding the SSX2 antigen, but downstream of the promoter region. General methods for constructing MIP vectors from conventional plasmid vectors are described in detail in Lu, J., Zhang, F. and Kay, M. A. (2013), A mini-intronic plasmid (MIP): a novel super-compact expression vector in vivo and in vitro, *Mol Ther* 21: 954-63; and U.S. Patent Publication 2013/0210897, each of which is incorporated by reference herein in its entirety.

B. Using DNA Minicircle Vectors Prevents Gene Silencing and Facilitates Sustained Expression of the Polypeptide of Interest.

In these preliminary studies, we demonstrate that using vectors in a DNA vaccine delivery model having the plasmid backbone substantially deleted (i.e., DMCs) results in sustained expression of the polypeptide of interest, as compared to using conventional plasmids, where expression substantially decreases over time.

Cos-7 cells (immortalized simian CV-1 cells carrying SV40 virus genetic material) were transfected by equimolar amounts of conventional plasmid vectors encoding green fluorescent protein (GFP) as the polypeptide of interest (pMC-GFP), or DNA minicircle vectors encoding GFP as the polypeptide of interest (DMC-GFP). Cells were imaged using fluorescence microscopy at 24 hour intervals.

As seen in FIG. 2, after day 3, both cell populations exhibited robust expression of GFP (see left panel). However, at day seven, expression of GFP in cells transfected with the conventional plasmid (pMC-GFP) exhibited minimal GFP expression (top right), while cells transfected with the DNA minicircle vectors (DMC-GFP) maintained substantial expression of GFP (bottom right).

These results suggest that deleting a substantial portion of the plasmid backbone of the plasmid designed to deliver a DNA vaccine is an effective strategy for preventing gene silencing and for maintaining expression of the polypeptide of interest. The related strategy of placing the primary elements of the plasmid backbone within an intron inserted into the expression cassette (i.e, the use of MIPs) is explored further below.

C. Both Antigen-Encoding DNA Minicircle Vectors and Antigen-Encoding Mini-Intronic Plasmid Vectors Prevent Gene Silencing in an In Vitro DNA Vaccine Model, while Antigen-Encoding Mini-Intronic Plasmids Exhibit the Highest Level of Antigen Expression.

To further explore the effect of the vector type used on expression levels of the antigen of interest in DNA vaccine models, we prepared 3 different DNA vectors coding for the SSX2 antigen (a conventional plasmid (pTVG), a DNA minicircle (DMC), and a mini-intronic plasmid (MIP)), as well as a control vector lacking an SSX2 coding region (pTVG4), as described above. Androgen-sensitive human prostate adenocarcinoma (LNCaP) cells were transfected with equimolar amounts of pTVG, DMC, MIP, or pTVG4 control. Cells were lysed after 2 or 7 days, and enzyme-linked immunosorbent assay (ELISA) was used to determine the amount of SSX2 antigen present in the lysate.

As shown in FIG. 3A, after seven days, the DMC and the MIP vectors both achieved significantly greater SSX2 expression than the conventional pTVG plasmid (see right panel). Notably, after seven days, SSX2 expression was highest for MIP vector (see right panel), and after two days, SSX2 expression was significantly higher for the MIP vector than for either the DMC vector or the conventional pTVG plasmid (see left panel). These results confirm that using DNA vectors in which the plasmid backbone is removed (DMC) or inserted as an intron into the expression cassette (MIP) as DNA vaccines facilitates sustained expression of the antigen of interest. Furthermore, the results suggest that, in addition to ease of synthesis and use, using MIP vectors in DNA vaccines may have further advantages over using DMCs, such as increased levels of expression of the desired antigen.

In vivo studies showed persistent expression of the transgene. Equimolar amounts of pTVG-SSX2 and MIP-SSX2 were injected intradermally in the ear of mice (n=2 per group) using a 28.5 gauge needle. The injection site was excised after 48 h and RNA was extracted from the tissue using standard methods. Levels of antigen mRNA were assayed by quantitative reverse-transcriptase PCR. Fold change values were calculated over background (detection levels in tissue from untreated mice). As shown in FIG. 3B, use of MIP led to persistent expression of SSX2.

D. Antigen-Encoding Mini-Intronic Plasmid Vectors Facilitate B Cell Mediated T Cell Expansion In Vitro.

We next assayed the extent of SSX2-specific CD8+ T cells expansion facilitated by two different cell and vector types. CD11c+ dendritic cells and CD19+ B cell populations were enriched using STEMSEP® anti-phycoerythrin (PE) selection and incubated with T-lymphocytes from an HLA-A2+ patient known to have CD8+ T cells specific for HLA-A2-restricted p41 and p103 SSX2-specific epitopes. These cells were then treated with either a DNA vector control (pTVG4), or a mini-intronic plasmid encoding SSX2 (MIP-SSX2), along with 0.5 ng/mL IL-1β and 10 U/mL IL-2 for 7 days, after which tetramer staining was performed.

FIG. 4 shows the results of the assay. These data demonstrate that using the MIP vector facilitates substantial B cell-facilitated expansion of mature antigen-specific CD8+ T cells, as compared to using the pTVG4 plasmid control. These results suggest that MIP DNA vectors can function as DNA based vaccines, be presented by professional antigen presenting cells (APCs) and expand a population of antigen specific T cells.

E. Antigen-Encoding DNA Minicircle Vectors Facilitate Improved Antigen-Specific T Cell Production In Vivo.

To explore the effects of vector type in an in vivo DNA vaccine model, we immunized HHD-II mice four times at 2-week intervals with a conventional DNA plasmid encoding SSX2 (pTVG-SSX2), a DNA minicircle encoding SSX2 (DMC-SSX2), or vector control (pTVG4). Splenocytes were collected, pooled, and assessed for the frequency of SSX2 tetramer-specific CD3+CD8+ gated T cells (p103=dominant epitope, p41=subdominant epitope, pp11=control). As illustrated in FIG. 5, immunization with the DNA minicircle vector elicited the highest frequency of antigen-specific CD8+ T cells.

We also assayed SSX2 epitope-specific IFNγ release in the splenocytes collected from the immunized mice. Androgen receptor-specific IFNγ release (pAR) was assayed for comparison purposes, as a negative control. The results are illustrated in FIG. 6. Once again, the results show that using a DNA vector having the deleted plasmid backbone (the DMC) elicits a substantially stronger immune response than using a conventional plasmid.

Taken together, the data disclosed in this Example suggests that using DMC or MIP-based plasmids will result in improved DNA vaccines showing improved efficacy.

Example 2

Protection Study

Prophylactic MIP-SSX2 immunization is shown to protect against subsequent tumor challenge in the mouse tumor model. FIG. 7 is a schematic diagram illustrating the tumor model study design used (bottom) with the prophylactic study demonstrating protection against subsequent tumor challenge. HLA-A2 expressing mice were first immunized four times (day 0, 13, 26, 39) at 2-week intervals with MIP-SSX2, pTVG-SSX2 or pTVG4 and subsequently challenged with 5*10$^4$ A2/Sarcoma cells expressing SSX2 on day 52 to assay for anti-tumor efficacy of the different constructs. The average tumor volume after immunization with prophylactic MIP-SSX2 or plasmid DNA encoding SSX2 (pTVG-SSX2) was monitored over time and the results are depicted in FIG. 8A. FIG. 8B is a graph depicting the frequency of tetramer CD8+ T cells after prophylactic immunization.

Example 3

MIP DNA Vaccines are Less Effective at Shrinking Tumors than Conventional Plasmid DNA Vaccines, Because of Unexpected MIP-Facilitated Upregulation of LAG-3

In this Example, we used an in vivo sarcoma tumor model to compare the efficacy of a DNA vaccine delivered using a conventional plasmid vector to the efficacy of a DNA vaccine delivered using a mini-intronic plasmid vector. Based on the results of Example 1, we expected that the DNA vaccine delivered using the mini-intronic plasmid would be more effective at reducing the size of the induced tumors. Surprisingly, we found that DNA vaccines delivered using conventional DNA plasmids had greater anti-tumor efficacy than DNA vaccines delivered using mini-intronic plasmids. Upon further investigation, we found that delivering DNA vaccines using mini-intronic plasmids upregulated the immunoinhibitory checkpoint protein LAG-3 on CD8+ T cells, whereas delivering DNA vaccines using conventional plasmids did not upregulate LAG-3. We also found that other immune system inhibitors were not upregulated by delivering DNA vaccines using mini-intronic plasmids. Based on these results, to maximize the anti-tumor efficacy of DNA vaccines delivered using mini-intronic plasmids, a LAG-3 blocking agent should administered with the DNA vaccine. By blocking the immunoinhibitory effects of the upregulated LAG-3, the LAG-3 blocking agent would synergistically improve the efficacy of such DNA vaccines.

As shown in FIG. 7, on Day 0 of the tumor model study, we subcutaneously implanted HLA-A2 expressing mice with 10$^5$ A2/Sarcoma cells expressing SSX2. We subsequently immunized the mice two times at 2-week intervals (on Days 1 and 15) with plasmid DNA encoding SSX2 (pTVG-SSX2), mini-intronic plasmid DNA encoding SSX2 (MIP-SSX2), or vector control (pTVG4). Tumor growth was measured volumetrically three times a week during the twenty seven day period following implantation.

As seen in FIGS. 9A and 9B, mice immunized with MIP-SSX2 exhibited significantly greater tumor growth than mice immunized with pTVG-SSX2. These results suggest that a factor related to the type of plasmid used to deliver the DNA vaccine was decreasing the anti-tumor efficacy of the MIP-delivered DNA vaccine.

We next measured LAG-3, TIM-3 and PD-1 expression data for CD8+ tumor infiltrating lymphocytes (TILs) obtained from mice immunized with plasmid DNA encoding SSX2 (pTVG-SSX2), mini-intronic plasmids encoding SSX2 (MIP-SSX2), or vector control (pTVG4). Surprisingly, we found that CD8 TILs from MIP-treated animals displayed elevated levels of LAG-3, a cell surface immune checkpoint protein associated with immunotolerance and anergy (FIG. 10A). Other regulatory markers on CD8 TILs (FIGS. 10B and 10C) and CD4 TILS (data not shown) remained unchanged. These data show that increased LAG-3 expression in mice immunized with MIP DNA vaccines likely explains the tumor growth results shown in FIGS. 9A and 9B. Thus, co-administration of a LAG-3 blocking agent would lead to reduced tumor growth in MIP-immunized animals.

In an experiment confirming that LAG-3 upregulation is a function of the vector type used to deliver the vaccine, rather than being tumor-dependent, we used flow cytometry to obtain LAG-3 expression data for splenocytes from naïve animals previously immunized with another sustained expression vector, DMC-SSX2, which was described above. Splenocytes from the previously immunized naïve animals were stained with p41 and p103 tetramers (to identify SSX2 antigen specific T cells) and analyzed for levels of LAG3. P41 and p103 specific cells from non-tumor-bearing mice that were immunized with DMC-SSX2 had elevated levels of LAG3, in comparison to mice that were immunized with conventional plasmid vector pTVG-SSX2 (FIG. 11).

These data establish that the elevated levels of LAG-3 expression exhibited by TILs from MIP-SSX2 immunized animals (see FIG. 10) was the result of using a sustained expression type of vector for DNA vaccine delivery, rather than being caused by the tumor targeted by the DNA vaccine. Accordingly, delivering DNA vaccine using a MIP vector, in combination with administering a LAG-3 blocking agent, will synergistically increase the effectiveness of a wide range of DNA vaccines.

Not to be bound by any theory, but as galectin-3 suppression of LAG3 is only active in the tumor microenvironment (See, e.g., Kouo et al. (2015). Galectin-3 Shapes Antitumor Immune Responses by Suppressing CD8+ T Cells via LAG-3 and Inhibiting Expansion of Plasmacytoid Dendritic Cells. Cancer Immunol Res 3, 412-423), an inhibitor of Galectin-3 may increase CD8+ response against tumors if used in conjunction with a DNA vaccine specifically targeting the tumor antigen. It is contemplated that other inhibitors or antibodies that bind and disrupt other proteins or ligands within the LAG-3 pathway can be used synergistically in conjunction with MIP DNA vaccines to provide tumor growth suppression.

Example 4

Improved Immune Response Using MIP Vaccine when Combined with a LAG-3 Blocking Agent The anti-tumor effects of MIP-SSX2 immunization can be rescued by combination with anti-LAG-3 antibody (αLAG3). HLA-A2-expressing mice (average of n=6 per group) were implanted subcutaneously with A2/Sarcoma cells and immunized bi-weekly with plasmid DNA encoding SSX2 (pTVG-SSX2), mini-intronic plasmids encoding SSX2 (MIP-SSX2), or vector control (pTVG4) alone or in combination with 200 μg of a monoclonal antibody against murine LAG3 (clone C9B7W, BioXCell) administered 24 h and 72 h after vaccination. Tumor growth was measured by volumetric measurements 3 times a week. FIG. 12 is a graph showing tumor growth as a function of time. FIG. 13 is a graph that shows individual tumor growth curves for each animal treated with MIP-SSX2 alone. FIG. 14 shows individual tumor growth curves for each animal treated with MIP-SSX2 in combination with LAG3 blockade.

MIP-SSX2 in combination with αLAG3 is superior to plasmid DNA vaccination alone. Mice were treated as described above. FIG. 15 shows individual tumor growth curves of groups treated with pTVG-SSX2 alone (red) or the MIP-SSX2+aLAG3 combination (blue). The MIP-SSX2+aLAG3 combination resulted in a complete elimination of established tumors, showing a synergy of the 2 treatments above what is expected from a DNA vaccine (PTVG-SSX2). Complete response (CR) is no tumor detectable upon dissection.

This data shows a reduced activity of LAG3 expressing T cells in vivo in the tumor microenvironment. The tumor microenvironment is known to be suppressive in many ways (Rabinovich, G. A., Gabrilovich, D., and Sotomayor, E. M. (2007). Immunosuppressive Strategies that are Mediated by Tumor Cells. Annual Review of Immunology 25, 267-296). This is a novel finding as it is not expected that a vector that elicits more T cells and protects against subsequent tumor cell challenge does not work as well in a therapeutic setting.

Example 5

Improvement of MIP Vaccine by the Inhibition of Galectin

The ability to block a binding partner of LAG-3 will also improve the immune response against a MIP vaccine comprising the antigen of interest. Experiments similar to Example 3 using anti-LAG-3 will be performed using an anti-Galectin-3 inhibitor, N Acetyl D Glucosamine (GlcNAc). Animals will be placed into the following groups to be tested: pTVG4+vehicle, PTVG-SSX2+vehicle, MIP-SSX2+vehicle, pTVG4+ GlcNAc, and MIP+ GlcNAc. Tumors will be implanted in A2 expressing mice on Day 1, and vaccination with the respective DNA constructs will begin on Day 2. For the entire treatment period, 100 micrograms of N Acetyl D Glucosamine (GlcNAc) or Water vehicle control will be administered to mice every 48 h. Growth will be monitored as described above.

Results should show that treatment with GlcNAc can rescue the MIP vaccine by improving the immune response and inhibiting the LAG-3 protein blocking pathway.

Each publication, patent, and patent publication cited in this disclosure is incorporated in reference herein in its entirety. The present invention is not intended to be limited to the foregoing examples, but encompasses all such modifications and variations as come within the scope of the appended claims.

We claim:

1. A method for reducing the number of cancer cells in a subject, the method comprising:
   administering to the subject a mini-intronic plasmid (MIP) comprising an expression cassette comprising (a) a polynucleotide sequence encoding an antigen expressed by the cancer cells, wherein the antigen is selected from the group consisting of synovial sarcoma x breakpoint 2 (SSX2), androgen receptor ligand-binding domain (AR LBD), prostate-specific antigen (PSA), human epidermal growth factor receptor 2 (HER-2/neu), and prostatic acid phosphatase (PAP), and (b) an intron containing a bacterial origin of replication and a selectable marker, whereby antigen-specific CD8+ T cells are activated against the cancer cells; and
   administering to the subject an antibody that binds to lymphocyte activation gene 3 (LAG-3), whereby the antibody reduces immunoinhibitory effects of increased LAG-3 expression in tumor infiltrating lymphocytes, relative to immunoinhibitory effects observed if no antibody is administered;
   whereby the number of cancer cells is decreased in the subject.

2. The method of claim 1, wherein the antibody to LAG-3 and MIP are co-administered simultaneously.

3. The method of claim 1, wherein the intron is located in the expression cassette upstream of the polynucleotide sequence encoding for the antigen.

4. The method of claim 1, wherein the method is performed without administering a programmed cell death protein 1 (PD-1) immune checkpoint protein blocking agent.

5. The method of claim 1, wherein the antigen is SSX2.

6. The method of claim 1, wherein the cancer is prostate cancer.

* * * * *